United States Patent [19]

Konishi et al.

[11] Patent Number: 5,124,150
[45] Date of Patent: Jun. 23, 1992

[54] PROCESS FOR PREPARING ANTIVIRAL ANTIBIOTIC BU-3889V

[75] Inventors: Masataka Konishi, Kawasaki; Mitsuaki Tsunakawa, Yokohama; Osamu Tenmyo, Yokohama; Takeo Miyaki, Yokohama; Toshikazu Oki, Yokohama, all of Japan

[73] Assignee: Bristol-Myers Squibb Co., New York, N.Y.

[21] Appl. No.: 624,029

[22] Filed: Mar. 11, 1991

Related U.S. Application Data

[60] Division of Ser. No. 546,463, Jul. 6, 1990, which is a continuation-in-part of Ser. No. 536,746, Jun. 14, 1990, which is a continuation-in-part of Ser. No. 377,036, Jul. 10, 1989.

[51] Int. Cl.$^5$ .................. C12R 1/01; A61K 35/00; C12N 1/20
[52] U.S. Cl. .................. 424/116; 424/85.8; 424/114; 424/115; 424/117; 424/195.1; 435/74; 435/169; 435/252.1; 435/822; 514/25
[58] Field of Search .......... 435/169, 822, 74, 252.1; 424/195.1, 85.8, 114–117; 514/25

[56] References Cited

U.S. PATENT DOCUMENTS 4,920,215  4/1990  Holdom et al. .................. 435/886

Primary Examiner—Herbert J. Lilling
Attorney, Agent, or Firm—Ron K. Levy; David M. Morse; D. Mezzapelle

[57] ABSTRACT

Production of an antiviral antibiotic complex, BU-3889V and its bioactive components $A_1$, $A_2$, $A_3$, $D_1$, $D_2$ and $D_3$, by fermentation of a BU-3889V producing strain of the new microorganism *Amycolatopsis orientalis* ATCC-53884 is disclosed. Complex BU-3889V is recovered and the components separated by the use of ion exchange chromatography techniques. The bioactive components are characterized by their physico-chemical characterizing properties. The products have been found to be effective to inhibit viruses including herpes simplex virus, human immunodeficiency virus (HIV) and influenza virus.

7 Claims, 16 Drawing Sheets

HPLC CHROMATOGRAMS OF BU-3889V COMPONENTS

HPLC CONDITION

COLUMN : CAPCELL PAK C18 (4.6 × 150 mm, 5 μm, SHISEIDO)
MOBILE PHASE : MeOH–0.05M Sörensen buffer, pH 8.0, 30 – 55% GRADIENT
FLOW RATE : 1.2 ml/min
DETECTION : UV ABSORPTION AT 254 nm.

BU-3889V A MIXTURE $A_3$ (Rt 4.2)
$A_2$ (Rt 6.8)
$A_1$ (Rt 11.6)

HPLC CHROMATOGRAMS OF BU-3889V D MIXTURE

HPLC CONDITION

COLUMN : CAPCELL PAK C18 (4.6 x 150 mm, 5 μm, SHISEIDO)
MOBILE PHASE : MeOH-0.05M Sörensen buffer, pH 8.0
30 - 55% GRADIENT
FLOW RATE : 1.2 ml/min
DETECTION : UV ABSORPTION AT 254 nm.

PROCESS FOR PREPARING ANTIVIRAL ANTIBIOTIC BU-3889V

This application is a division of co-pending application Ser. No. 546,463 filed on Jul. 6, 1990 which was a continuation-in-part of co-pending application Ser. No. 536,746 filed on Jun. 14, 1990 which was a continuation-in-part of 377,036 filed Jul. 10, 1989.

BACKGROUND OF THE INVENTION

Field of the Invention

This invention relates to a new antiviral antibiotic complex and its components. It relates also to methods of producing the novel products utilizing novel strains of the species *Amycolatopsis orientalis*, to their use as antiviral agents and to pharmaceutical compositions containing them.

SUMMARY OF THE INVENTION

This invention is a new water soluble antiviral antibiotic complex designated BU-3889V, and its antibiotically active components which are produced by fermenting a BU-3889V producing strain of *Amycolatopsis orientalis* ATCC-53884 or a mutant thereof, in an aqueous fermentation culture nutrient medium containing assimilable sources of nitrogen and carbon under submerged aerobic conditions until a substantial amount of the antibiotic complex of BU-3889V is produced by the organism in the fermentation culture nutrient medium. The antibiotic components produced by the above identified organism are recovered by separating the water-insoluble material from the fermentation broth to obtain a fermentation supernatant liquid containing the water soluble antibiotic activity from which the novel antibiotic complex and its components are isolated by chromatographic techniques.

DETAILED DESCRIPTION OF THE INVENTION

Figure 1:
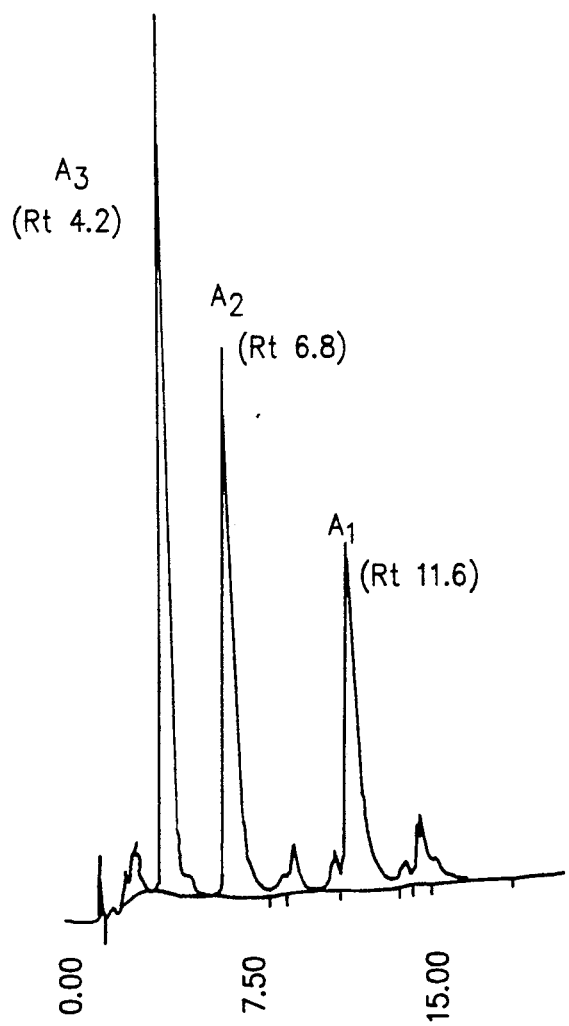
FIGS. 1 to 5 show the high pressure liquid chromatography (HPLC) scan of the BU-3889V complex and of components $A_1$, $A_2$, $A_3$, and $D_1$, respectively.
Figure 2:
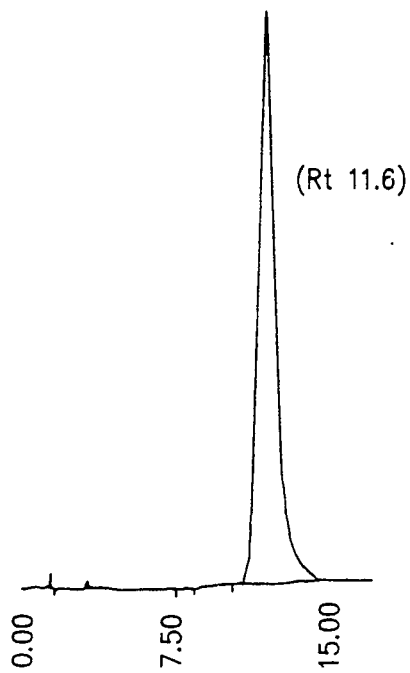
Figure 3:
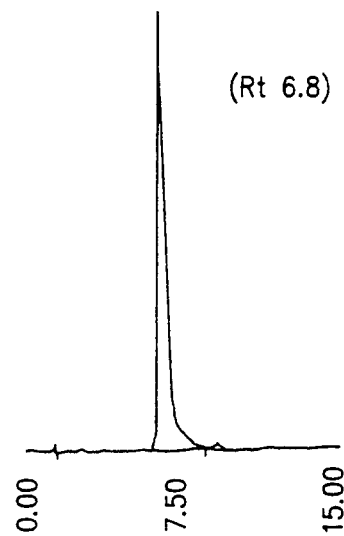
Figure 4:
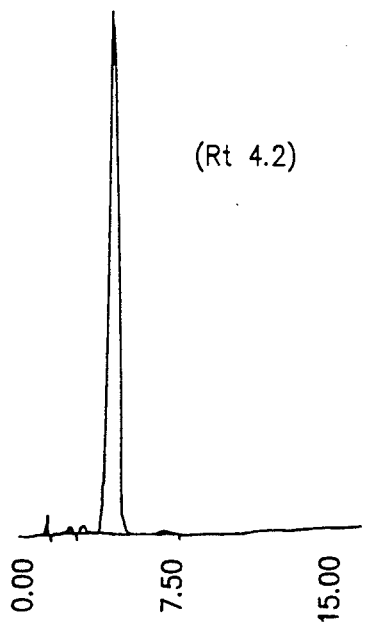
Figure 5:
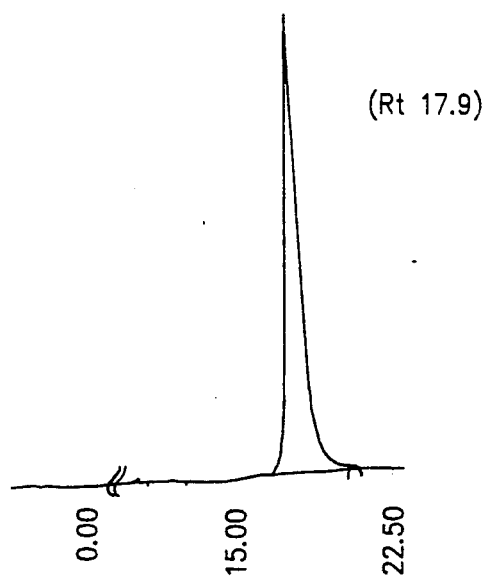
Figure 6:
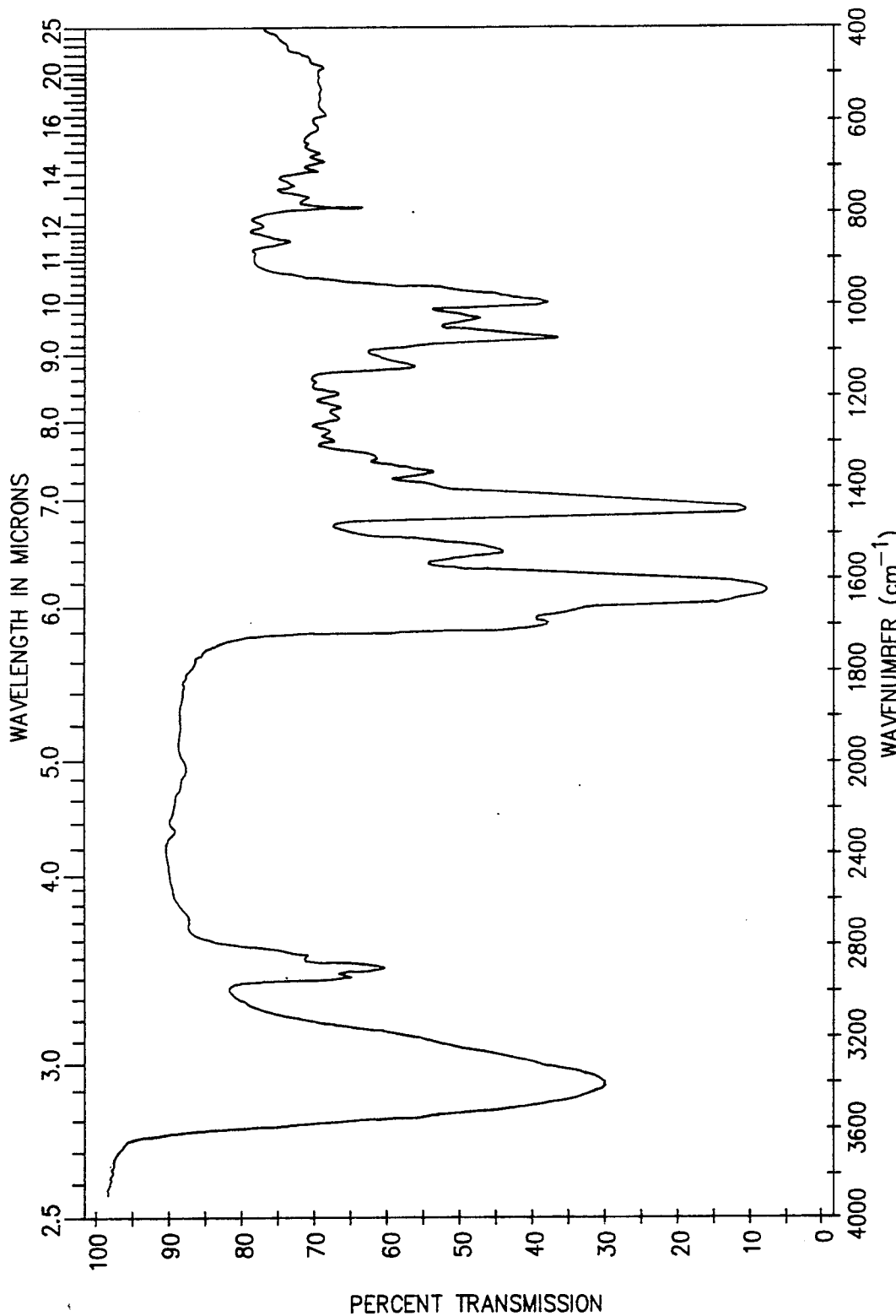
FIGS. 6 to 9 show the infrared (IR) absorption spectrograph of components $A_1$, $A_2$, $A_3$, and $D_1$ in a potassium bromide pellet.
Figure 7:
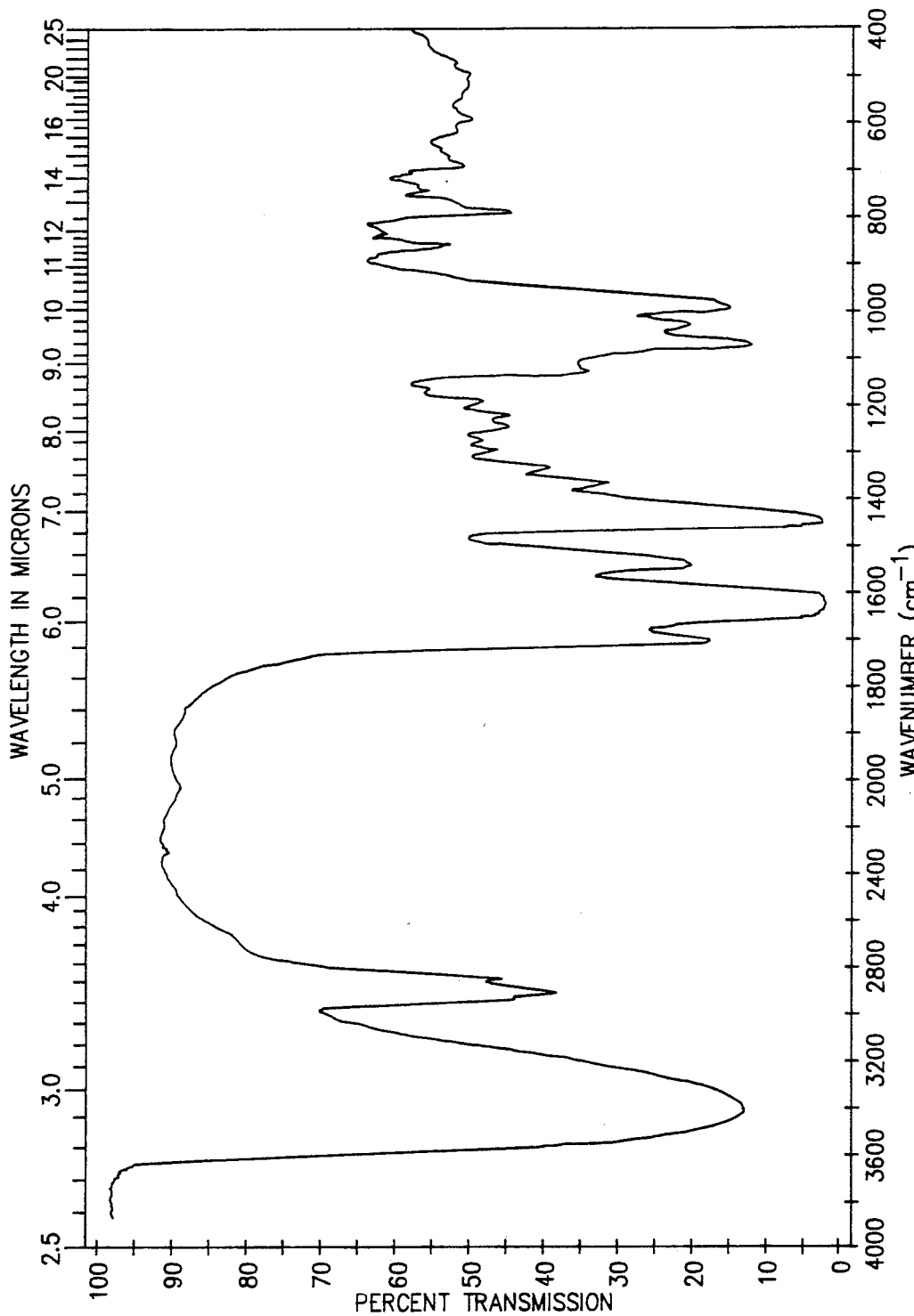
Figure 8:
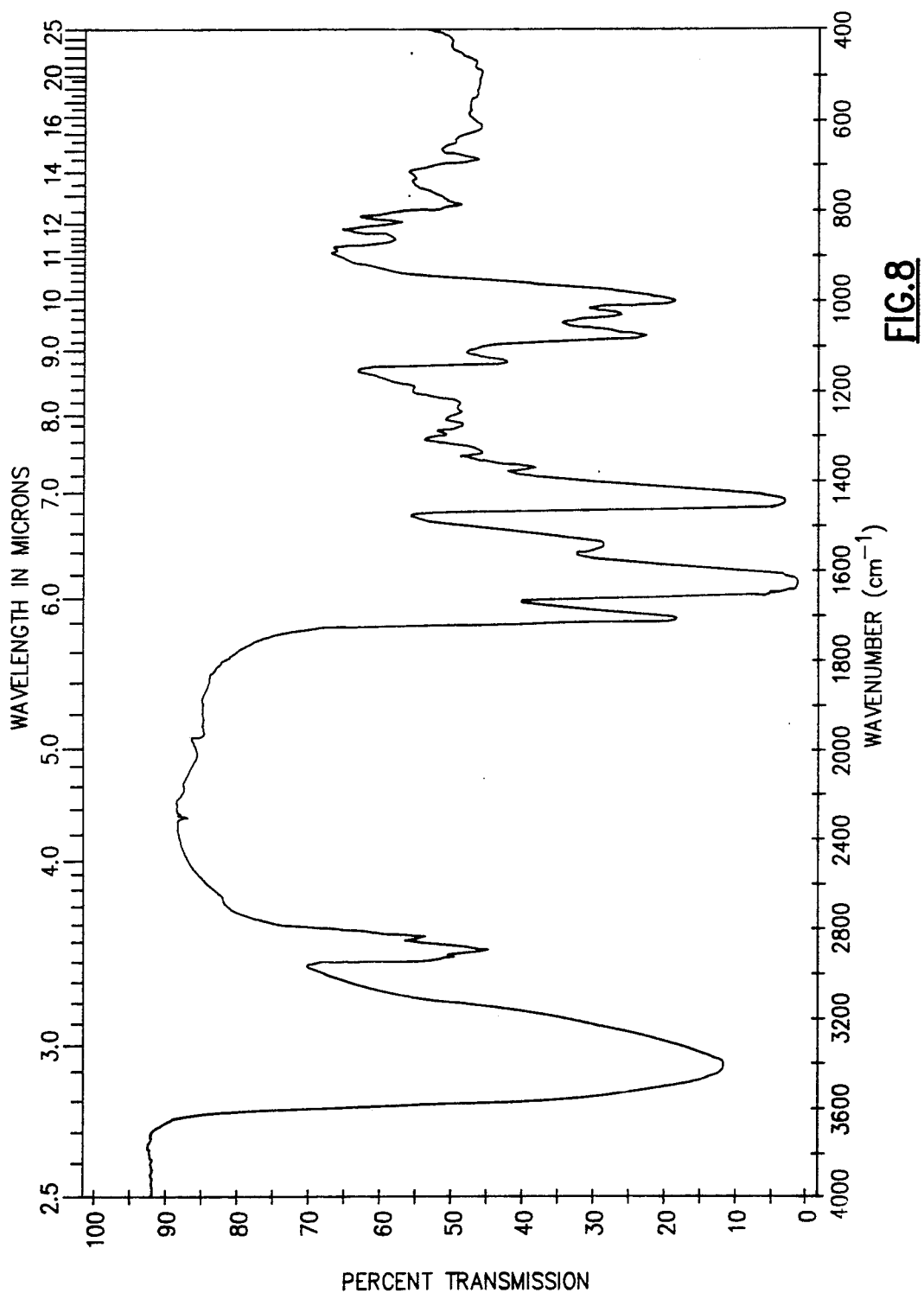
Figure 9:
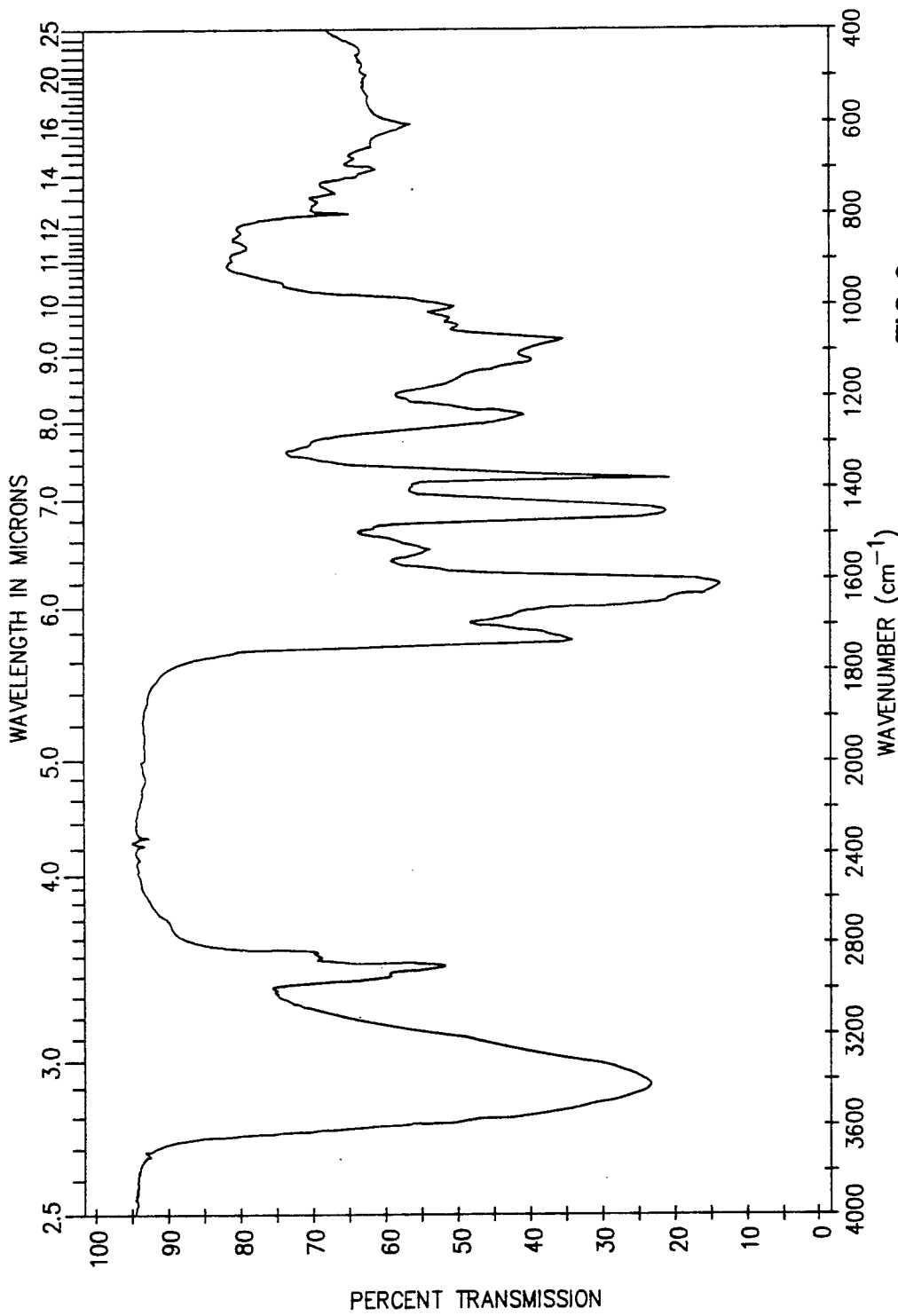

In one aspect, the present invention is a new antiviral antibiotic complex, designated BU-3889V, which is produced by fermenting a BU-3889V producing strain of *Amycolatopsis orientalis*, most preferably the strain *Amycolatopsis orientalis* ATCC-53884.

In another aspect, the invention includes the antiviral components BU-3889V $A_1$, BU-3889V $A_2$, BU-3889V $A_3$, BU-3889V $D_1$, BU-3889V $D_2$ and BU-3889V $D_3$, isolated from the complex.

In another aspect, the invention includes pharmaceutical compositions containing the complex or at least one of the components together with a pharmaceutically acceptable excipient.

In another aspect, the invention includes a process for producing and isolating the novel aforesaid products.

In still another aspect, the invention includes a process for inhibiting the growth of viruses comprising contacting such viruses with a growth inhibitory effective amount of one or more of the novel products of the invention.

In yet another aspect, the invention is the novel microorganism *Amycolatopsis orientalis* ATCC-53884 as provided by the present invention in the form of a biologically pure culture.

The new culture Amycolatopsis orientalis Q427-8 was submitted to the American Type Culture Collection, Rockville, Md., and given the designation ATCC-53884. The permanency of the deposit of this culture at The American Type Culture Collection at Rockville, MD, and ready accessibility thereto by the public are afforded throughout the effective life of the patent in the event the patent is granted. Access to the culture is available during pendency of the application under 37 C.F.R. 1.14 and 35 U.S.C. 112. All restrictions on the availability to the public of the culture deposited will be irrevocably removed upon granting of the patent.

The Microorganism

1. Taxonomy

An actinomycete, strain ATCC-53884, which produces the antiviral antibiotic BU-3889V complex was isolated from a soil sample collected in Maharastra State, India. The morphological, cultural and physiological characteristics, and cell chemistry of strain ATCC-53884 indicate that the strain is classified as *Amycolatopsis*, a genus of nocardioform actinomycetes. Based on the diagnostic physiological characteristics, it is a strain of *Amycolatopsis orientalis*.

2. Morphology

Substrate and aerial hyphae are long, monopodially branched, and partially zigzag-shaped. Partial fragmentation of substrate hyphae occurs at the periphery of intact colony after incubation for 3 weeks. The aerial hyphae bear long straight chains of oblong spores ($0.6 \times 0.6 - 3.0$ m) with a smooth surface.

Motile spores, sporangia, or synnemata are not formed.

3. Cultural and Physiological Characteristics

The colorless or yellowish colony is covered with white aerial mycelium. Carotinoid yellow pigment is formed, but melanoid and other distinct pigments are not formed.

The temperature range for growth is 19° C. to 40° C. Among 25 sugars examined, acid production is observed in 22 sugars, but not with D-melezitose, cellulose, and dulcitol.

The cultural characteristics are shown in Table i. The diagnostic physiological characteristics (Table 2) which were determined are based on the methods of Gordon, et al., J. Gen. Microbiol., 109, pp. 69-78, 1978, and Lechevalier, et al., Int. J. Syst. Bacteriol., 36, pp. 29-37, 1986.

4. Chemotaxonomy

Whole cell hydrolysate contains meso-diaminopimelic acid, galactose, arabinose, and rhamnose. Hence, the cell wall belongs to Type IV$_A$. Phospholipids contain phosphatidylethanolamine which showed 2 spots on thin layer chromatography (TLC), phosphatidylglycerol, and phosphatidylinositol. Therefore, the strain belongs to Type P-II. Glycolate test is negative (N-acyl type of peptidoglycan: acetyl). Mycolic acid is absent, and menaquinone MK-9 (H$_4$) is observed as a major component.

5. Taxonomic Position

Strain ATCC-53884 belongs to mycolateless nocardioform actinomycetes. Among 11 genera of nocardioforms, (see Lechevalier, et al., Loc. cit, and Lechevalier, et al., in Bergey's Manual of Systematic Bacteriology, Volume 2, pp. 1458-1506, 1986, Williams & Wilkins, Baltimore, Md.), strain ATCC-53884 is chemotaxonomically placed in Amycolatopsis which includes four species, *A. orientalis, A. orientalis* subsp. *lurida, A. mediterranei, A. rugosa,* and *A. sulphurea*. Physiological characteristics of strain ATCC-53884 indicate that the strain could be classified as *Amycolatopsis orientalis.*

TABLE 2-continued

| Physiological characteristics of strain ATCC-53884 | | | |
|---|---|---|---|
| Growth at: | | D-Fructose | + |
| 10° C. | − | D-Mannose | + |
| 45° C. | − | Salicin | +(w) |
| Acid produced | | Soluble starch | − |
| from: | | Sucrose | + |
| Adonitol | + | Temperature: | |
| D(−)Arabinose | + | Growth range | 19° C.-40° C. |
| | | Optimal growth | 25° C.-34° C. |
| | | No growth | 16° C. & 43° C. |
| | | Tolerance to: | |
| | | NaCl, 1%-8% | + |
| | | 9% | − |
| | | pH. 5.0-11.5 | + |

Abbreviations
TR: trace.
+(w): weakly positive.
ND: not determined

6. Partial Structures and NMR Spectra

The $^{13}$C-NMR (Nuclear Magnetic Resonance) spectra in Table 3 indicate 39 carbon signals in BU-3889V A$_1$ and 33 signals in BU-3889V D$_1$. The spectra of A$_1$ and D$_1$ correspond well except that resonances around δ 99.1, 72.0, 70.4, 70.3, 69.3, and 61.9 of BU-3889V A$_1$

TABLE 1

| Cultural characteristics of strain ATCC 53884 | | | | |
|---|---|---|---|---|
| Medium | Growth | Aerial mycelium | Reverse color | Pigment |
| Sucrose-nitrate agar (Czapek-Dox agar) | Moderate | Poor; white (263) | Light yellow (86) | None |
| Tryptone-yeast extract broth (ISP No. 1) | Moderate and not turbid | — | — | Pale yellow (89) |
| Yeast extract-malt extract agar (ISP No. 2) | Good | Abundant; white (263) | Brilliant orange yellow (67) | Light orange yellow (70) |
| Oatmeal agar (ISP No. 3) | Moderate | Moderate; white (263) | Colorless | None |
| Inorganic salts-starch agar (ISP No. 4) | Moderate | Moderate; white (263) | Vivid orange yellow (66) | Pale yellow (89) |
| Glycerol-asparagine agar (ISP No. 5) | Moderate | Moderate; white (263) | Pale yellow (89) | None |
| Peptone-yeast extract-iron agar (ISP No. 6) | Poor | No or scant; whitish | Colorless | None |
| Tyrosine agar (ISP No. 7) | Moderate | Moderate; white (263) | Pale yellow (89) | Pale yellow (89) |
| Glucose-asparagine agar | Poor | Poor; white (263) | Yellowish white (92) | None |
| Nutrient agar | Poor | Poor; white (263) | Colorless | None |

Observation after incubation at 28° C. for 3 weeks.
Color names: ISCC-NBS color-name charts

TABLE 2

| Physiological characteristics of strain ATCC-53884 | | | |
|---|---|---|---|
| Decomposition of: | | L(+)-Arabinose | + |
| Adenine | − | Cellobiose | + |
| Casein | + | Dextrin | ND |
| Hypoxanthine | + | Erythritol | + |
| Tyrosine | + | D-Galactose | + |
| Xanthine | + | D-Glucose | + |
| Decarboxylation of: | | Inositol | + |
| Benzoate | − | Lactose | + |
| Citrate | − or TR | Maltose | ND |
| Mucate | − | D-Mannitol | + |
| Succinate | + | D(+)-Melezitose | − |
| Tartrate | − or TR | Melibiose | + |
| Production of: | | α-Methyl-D- | + |
| Nitrate reductase | − | glucoside | |
| Amylase | +(w) | Raffinose | + |
| Urease | + | Rhamnose | + |
| Esculinase | + | Salicin | ND |
| Gelatinase | + | D-Sorbitol | + |
| Phosphatase | ND | Sucrose | ND |
| Tyrosinase | − | Trehalose | + |
| Growth on or in: | | D-Xylose | + |
| Lysozyme broth | − | Utilization of: | |
| Salicylate | ND | Cellulose | − |
| 5% NaCl | + | Dulcitol | − | are absent in BU-3889V D$_1$. Based on the $^1$H-NMR spectra (Table 4) and 2D-NMR analysis, these carbon signals are considered to be those of a galactopyranoside molecule.

Figure 12:
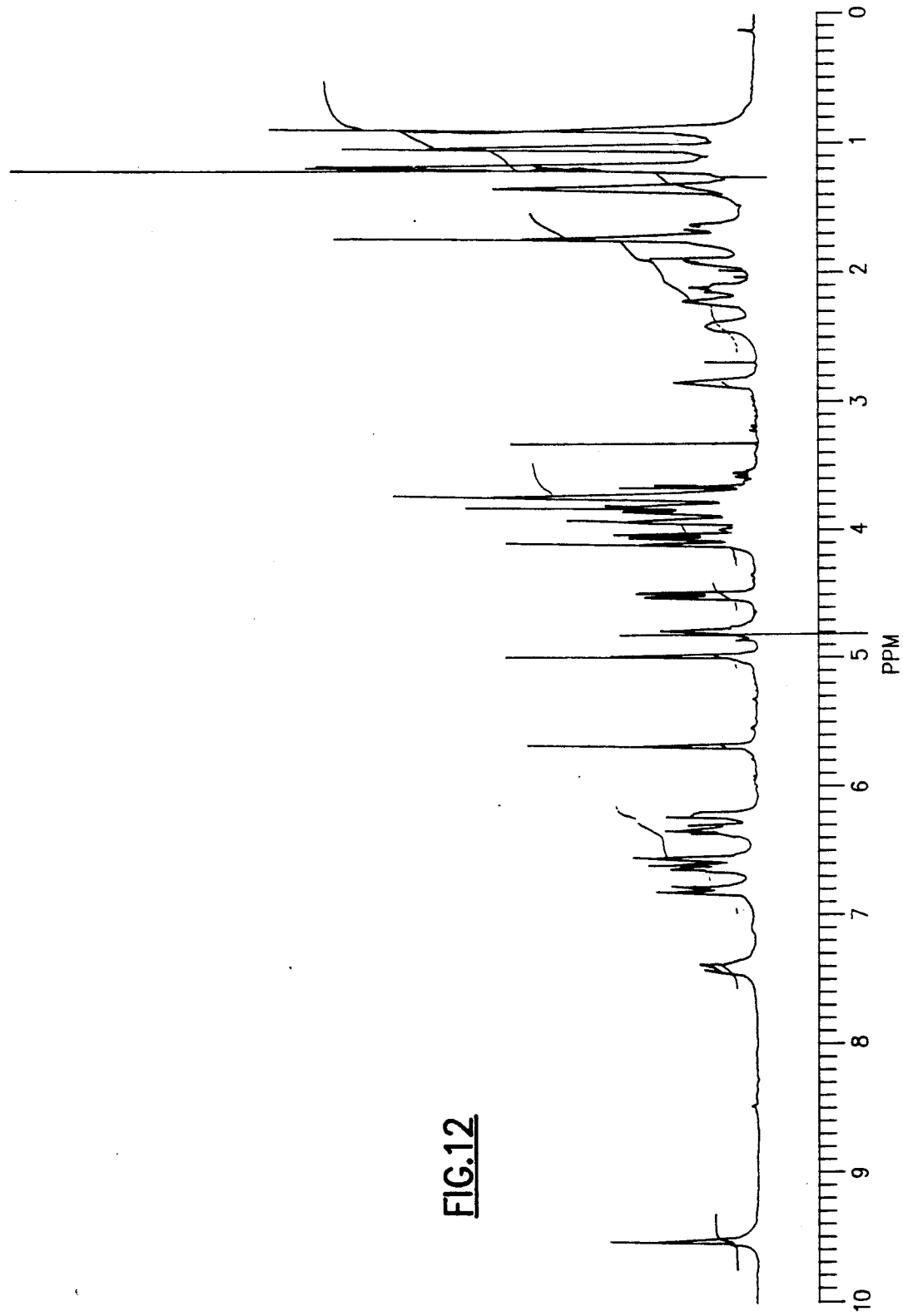
FIGS. 12 to 14 show the $^1$H-NMR spectra of $A_1$, $A_3$, and $D_1$, respectively.
Figure 13:
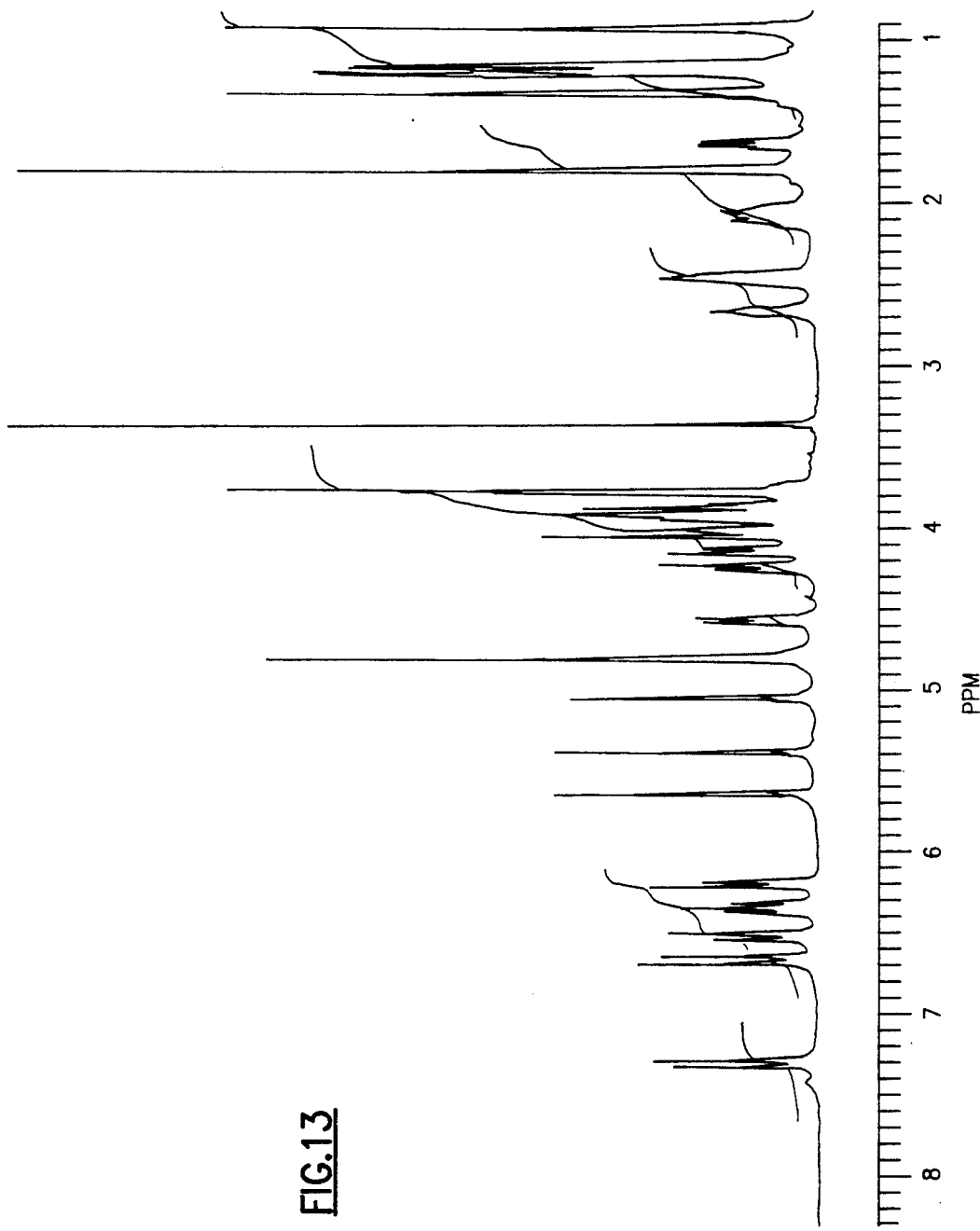
Figure 14:
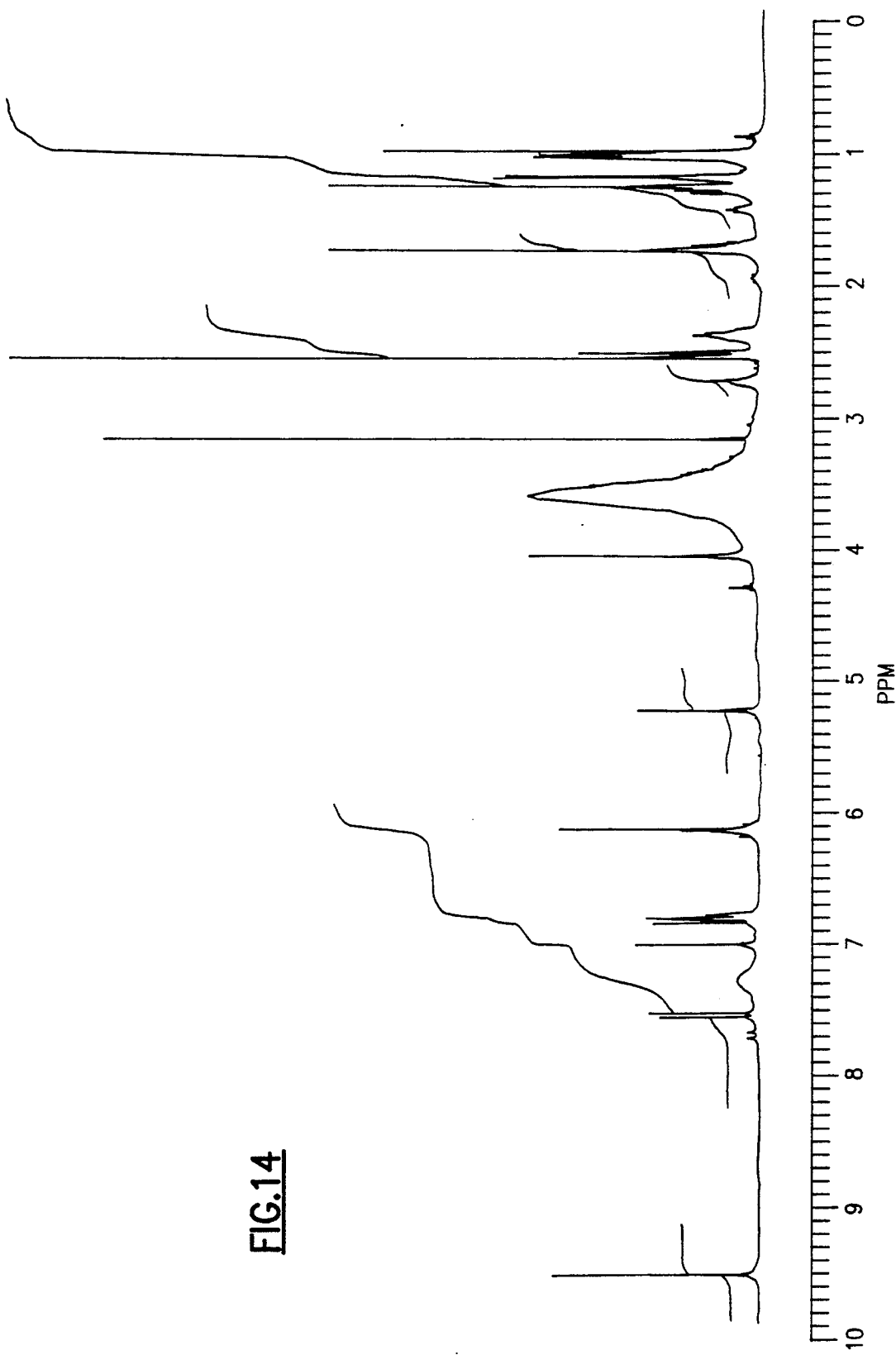

The $^1$H-NMR spectra taken at 400 MHz, D$_2$O, or DMSO-d$_6$ of A$_1$, A$_3$, and D$_1$ are shown, respectively, in FIGS. 12, 13, and 14.

Figure 15:
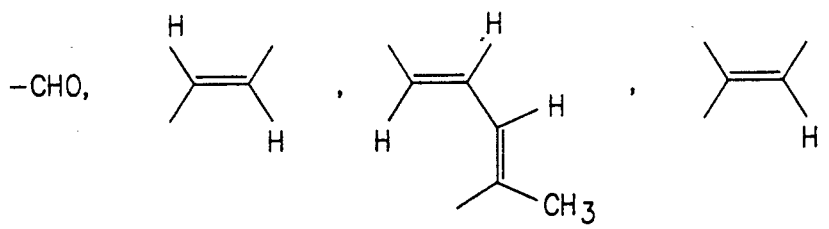
FIG. 15 shows some of the partial structure of $A_1$.
Figure 15:
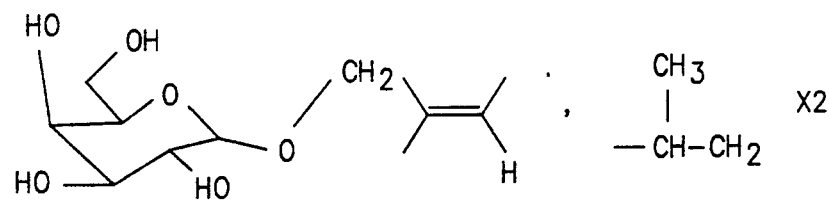
Figure 15:
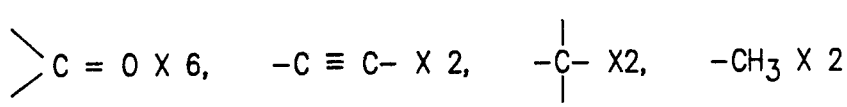
Figure 11:
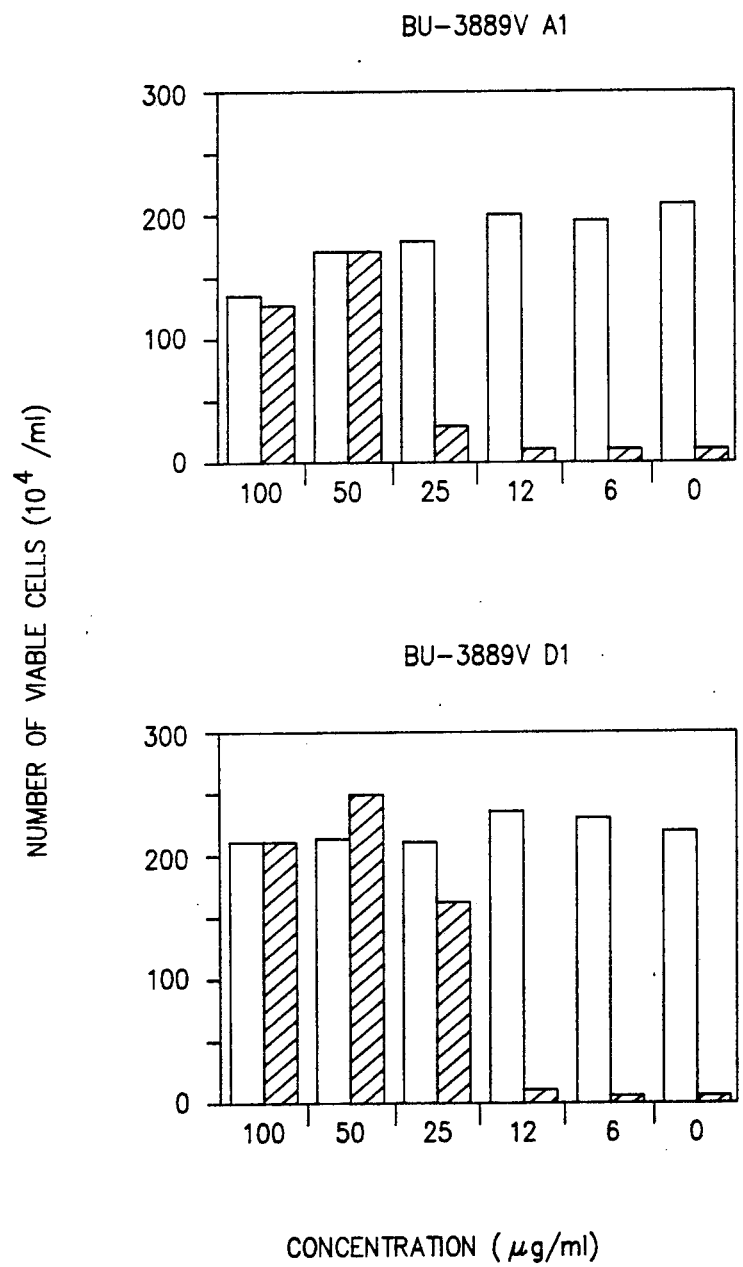
FIG. 11 shows the effect of $A_1$ and $D_1$ on cell growth of MT-4 Cells and the inhibition effect on the virus-induced cytopathic effects in HIV-infected MT-4 cells.

These findings suggest that A$_1$ is a galactoside derivative of D$_1$. In fact, upon mild acid methanolysis, A$_1$ yields D$_1$ and methyl D-galactoside. Extensive examination of the $^1$H-$^1$H COSY spectrum of A$_1$ reveals the presence of the partial structures shown in FIG. 15.

The molecular weights of BU-3889V A$_1$ and D$_1$ are assigned as 1504 and 1180, respectively, by negative fast atom bombardment mass spectrometry. The 324 mass unit difference between them corresponds to 2 moles of galactose. Interpretation of these data shows that BU-3889V A$_1$ is a dimeric structure of two 39 carbon compounds which are composed of the partial structures shown in FIG. 15. The $^1$H-and 13C-NMR spectra of BU-3889V A$_2$ and A$_3$ are very similar to those of BU-3889V A$_1$ differing only in the aldehyde signals. The spectra of BU-3889V A$_3$ lacks the aldehyde proton (δ:

9.50) and carbon signal (δ: 198.4) observed in those of BU-3889V $A_1$ but shows a hydroxymethyl signal ($^1$H.δ: 4.24 & 4.14 and $^{13}$C, δ: 65.1) which is not observed in BU-3889V $A_1$. The spectra of BU-3889V $A_2$ exhibits both the aldehyde and hydroxymethyl signals with about a half integration of those of other common signals. The spectral data suggest that BU-3889V $A_2$ and $A_3$ are reduced analogs of BU-3889V $A_1$ with one ($A_2$) or both ($A_3$) of the 2 aldehydes of the latter being reduced to —CH$_2$OH.

TABLE 3

| $^{13}$C-NMR data of BU-3889V $A_1$ and $D_1$ | | |
|---|---|---|
| Carbon | BU-3889V $A_1$ (D$_2$O) | BU-3889V $D_1$ (DMSO-d$_6$) |
| 1 | 199.3 s | 197.3 s |
| 2 | 198.4 d | 194.6 d |
| 3 | 198.2 s | 193.5 s |
| 4 | 196.7 s | 192.7 s |
| 5 | 183.7 s | 181.7 s |
| 6 | 177.1 s | 174.0 s |
| 7 | 176.8 s | 173.9 s |
| 8 | 157.5 d | 154.5 d |
| 9 | 145.6 d | 146.4 d |
| 10 | 143.4 d | 143.1 d |
| 11 | 143.2 s | 142.4 s |
| 12 | 137.9 s | 141.4 s |
| 13 | 137.8 d | 137.9 d |
| 14 | 135.3 s | 133.3 s |
| 15 | 132.7 d | 126.6 d |
| 16 | 130.3 d | 125.7 d |
| 17 | 127.6 d | 124.2 d |
| 18 | 99.9 s | 96.8 s |
| 19 | 99.1 d | — |
| 20 | 98.0 s | 93.7 s |
| 21 | 87.9 s | 85.0 s |
| 22 | 87.5 s | 83.3 s |
| 23 | 72.0 d | — |
| 24 | 70.8 t | 62.4 t |
| 25 | 70.4 d | — |
| 26 | 70.3 d | — |
| 27 | 69.3 d | — |
| 28 | 61.9 t | — |
| 29 | 45.7 s | 45.5 s |
| 30 | 45.4 s | 43.5 s |
| 31 | 36.6 t | 36.0 t |
| 32 | 32.8 t | 33.6 t |
| 33 | 28.7 d | 27.5 d |
| 34 | 25.5 d | 25.0 d |
| 35 | 22.8 q | 25.3 q |
| 36 | 22.5 q | 21.7 q |
| 37 | 20.9 q | 20.3 q |
| 38 | 18.5 q | 19.1 q |
| 39 | 12.6 q | 12.1 q |

TABLE 4

| $^1$H-NMR data of BU-3889V $A_1$ and $D_1$ (400 MHz) | |
|---|---|
| BU-3889V $A_1$ (D$_2$O) | BU-3889V $D_1$ (DMSO-d$_6$) |
| δ 9.50 (1H, s) | δ 9.52 (1H, s) |
| 7.38 (1H, d, J=15.8) | 7.52 (1H, d, J=15.4) |
| 6.78 (1H, d, J=15.8) | 6.99 (1H, s) |
| 6.61 (1H, d, J=14.7) | 6.80 (1H, d, J=15.8) |
| 6.54 (1H, br-s) | 6.77 (1H, d, J=11.6) |
| 6.31 (1H, dd, J=10.3 & 14.7) | 6.11 (2H, m) |
| 6.20 (1H, d, J=10.3) | 5.21 (1H, s) |
| 5.66 (1H, s) | 4.04 (2H, s) |
| 4.98 (1H, d, J=4.0) | 2.71 (1H, m) |
| 4.50 (1H, d, J=10.3) | 2.38 (2H, m) |
| 4.11 (1H, d, J=2.9) | 1.72 (3H, s) |
| 4.05 (1H, dd, J=3.3 & 10.3) | 1.68 (1H, m) |
| 3.93 (1H, t, J=6.2) | 1.41 (1H, m) |
| 3.86 (1H, d, J=10.3) | 1.27 (1H, m) |
| 3.82 (1H, dd, J=4.0 & 10.3) | 1.24 (3H, s) |
| 3.74 (2H, m) | 1.16 (3H, d, J=7.2) |
| 2.87 (1H, m) | 1.01 (3H, d, J=6.8) |
| 2.42 (1H, m) | 0.98 (3H, s) |
| 2.24 (1H, m) | |

TABLE 4-continued

| $^1$H-NMR data of BU-3889V $A_1$ and $D_1$ (400 MHz) | |
|---|---|
| BU-3889V $A_1$ (D$_2$O) | BU-3889V $D_1$ (DMSO-d$_6$) |
| 2.14 (1H, m) | |
| 1.93 (1H, m) | |
| 1.77 (3H, s) | |
| 1.66 (1H, d, J=15.8) | |
| 1.38 (3H, s) | |
| 1.20 (3H, d, J=7.3) | |
| 1.06 (3H, d, J=6.6) | |
| 0.92 (3H, s) | |

Figure 20:
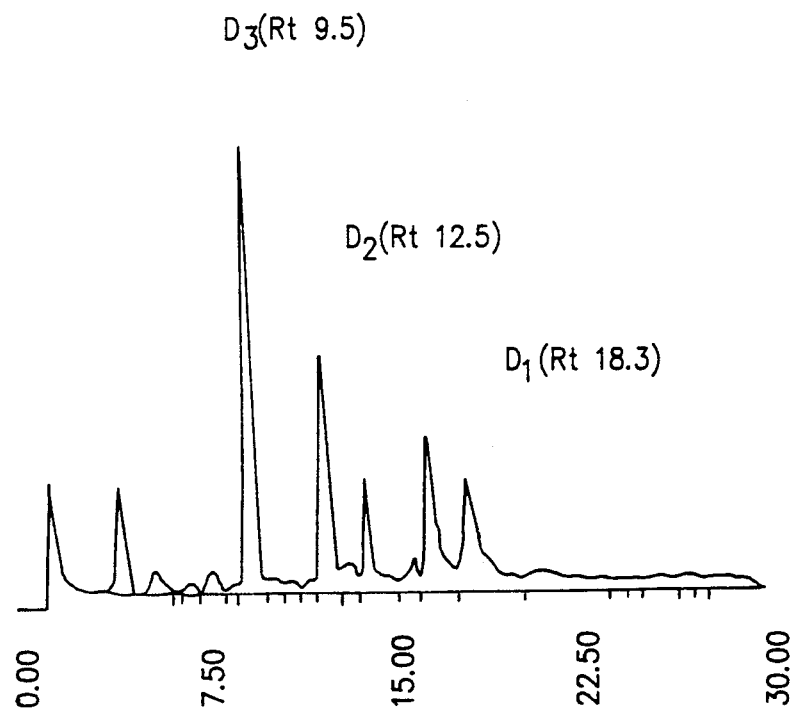
FIG. 20 shows the high pressure liquid chromatography (HPLC) scan of a mixture of BU-3889V $D_1$, $D_2$ and $D_3$ components.

Component BU-3889V $D_1$, subsequent to the filing date of parent application Ser. No. 377,036 filed Jul. 20, 1989, was found by HPLC to contain two additional components designated BU-3889V $D_2$ and BU-3889V $D_3$ in addition to BU-3889V $D_1$ (see FIG. 20). The physico-chemical and biological properties of these new component antibiotics are described below along with their methods of preparation.

Preparation, Isolation, and Purification of Antibiotic Products

The process for producing the antiviral antibiotic complex BU-3889V and the components $A_1$, $A_2$, $A_3$, $D_1$, $D_2$ and $D_3$ according to the present invention comprises the steps of:

(a) cultivating *Amycolatopsis orientalis* ATCC-53884 or a BU-3889V-producing variant or mutant thereof in an aqueous fermentation culture nutrient medium containing assimilable sources of nitrogen and carbon under submerged aerobic conditions until a substantial amount of the complex BU-3889V containing components designated $A_1$, $A_2$, $A_3$, $D_1$, $D_2$ and $D_3$ is produced by the organism in the fermentation culture medium;

(b) separating the mycelium and other undissolved residues from the fermentation culture medium to obtain a supernatant liquid which contains antibiotic activity;

(c) adsorbing the antivirally active components contained in the supernatant liquid from step (b) on a non-ionic ion exchange resin;

(d) separating the antivirally active components;

(e) adsorbing the antivirally active components on a silica gel column;

(f) separating and recovering the BU-3889V complex;

(g) separating and recovering the components $A_1$, $A_2$, $A_3$, $D_1$, $D_2$ and $D_3$ from the antiviral antibiotic complex, BU-3889V, by at least one conventional adsorption and crystallization technique.

The assimilable carbon source for use in the aqueous fermentation culture medium may be a carbohydrate such as, for example, glucose, ribose, galactose, fructose, mannose, sucrose, lactose, soluble starch, and glycerol, to name a few.

The assimilable nitrogen source for use in the aqueous fermentation culture medium may be any one of such conventionally known sources, including fish meal, soybean meal, corn steep liquor, peptones, meat extract, peanut flour, yeast extract, and ammonium salts to name but a few.

Inorganic salts, such as sodium chloride, potassium chloride, magnesium sulfate, calcium carbonate, phosphates, and the like, may be added if desired. In addition, trace elements, such as copper, manganese, iron, zinc, and the like, may be added if desired or they may be supplied as minor or trace impurities of other constituents in the fermentation media.

The incubation temperature may be any temperature at which a BU-3889V-producing strain is able to grow. Preferably, the incubation temperature is about 19°–40° C., more preferably about 25°–35° C., and most preferably about 27°–32° C.

A neutral or nearly-neutral initial pH, e.g. pH about 6–7, is preferably employed in the fermentation media, and production of the antibiotic complex by fermentation is generally carried out for a period of about 2–10 days. Ordinarily, optimum production is achieved in about 6–8 days. For the preparation of relatively small amounts of antiviral antibiotic complex, shake flasks and surface culture can be employed, whereas for relatively large amounts, submerged aerobic culture in sterile fermentation tanks is preferred. When tank fermentation is to be carried out, it is desirable to produce a vegetative inoculum in a nutrient broth by inoculating the broth culture with a spore from the organism and, when a young active vegetative inoculum has been obtained, transferring the inoculum aseptically to the fermentation tank medium. Aeration in tanks and bottles may be provided by forcing sterile air through or onto the surface of the fermentation medium. Further agitation of the medium may be provided by a mechanical impeller and an antifoaming agent such as is conventional in the art, e.g. lard oil, may be added as needed.

The production of the BU-3889V complex in the fermentation medium may be followed readily during the course of the fermentation by the dye-uptake assay with herpes simplex virus type I.

After optimum fermentation broth potency has been obtained (as determined by the above-described assay method), the mycelium and undissolved residues are separated from the fermentation broth by conventional means such as filtration and centrifugation to obtain a supernatant liquid (or filtrate) which contains antibiotic activity. The components having antibiotic activity can be recovered from the supernatant liquid by employing conventional adsorption techniques. The adsorbents which can be employed most advantageously are the nonionic macroreticular polymer resins including, for example, Diaion HP-20 resin (Diaion is a trademark owned by Mitsubishi Chemical Industries, Ltd., Tokyo, Japan) commercially available from Nippon Rensui Co., Japan.

In one preferred embodiment, the supernatant liquid, neutralized, if necessary to pH 7, is stirred with a nonionic resin such as Diaion HP-20 to adsorb the components having antibiotic activity from the supernatant liquid. These components include the BU-3889V complex and its $A_1$, $A_2$, $A_3$, $D_1$, $D_2$ and $D_3$ constituents. The resin is washed With water and a lower water miscible alkanol and the activity eluted with, e.g. aqueous acetone. Those effluents exhibiting activity in the dye-uptake assay are combined and concentrated in vacuo to an aqueous solution which is adjusted to pH 7.0, applied to a Diaion column and developed with water and lower alkanol. Evaporation of the bioactive alkanol eluates under reduced pressure to a concentrated aqueous solution followed by washing with a polar liquid such as an organic ester, and concentration of the aqueous layer under reduced pressure affords the crude BU-3889V.

Subsequent operations to obtain the $A_1$, $A_2$, $A_3$, $D_1$, $D_2$ and $D_3$ components are conducted in a dark room.

Preparation of BU-3889V $A_1$, BU-3889V $A_2$, BU-3889V $A_3$, BU-3889V $D_1$, BU-3889V $D_2$ and BU-3889V $D_3$ Components $A_1$, $A_2$ and $A_3$, in the presently preferred procedure, are obtained from the crude, solid BU-3889V by first combining the crude mixture with silica gel and loading the mixture on the top of a silica gel column (Wakogel C-200 brand silica gel commercially available from Wako Pure Chemicals Industries, Ltd., Japan) and eluting with a n-BuOH-n-PrOH-$NH_4OH$-$H_2O$ mixture. The selected fractions are monitored by the antiviral assay and TLC. They are concentrated under reduced pressure and the residue are dissolved in phosphate buffer (pH 7.0) and subjected to reversed phase $C_{18}$ column chromatography (YMC ODS, AM type, commercially available from Yamamura Chem. Lab. Co., Ltd., Japan). The column is developed with the same buffer containing increasing amounts of methanol. The eluate is followed with TLC. The first active fractions containing $A_3$ are concentrated to a small volume, and purified and isolated utilizing a Diaion HP-20 column. The second and third active eluates are similarly treated to obtain the $A_1$ and $A_2$ components. The $A_1$ component may be further purified by HPLC.

Preparation of BU-3889V $D_1$, BU-3889V $D_2$ and BU-3889V $D_3$

A mixture of $D_1$, $D_2$ and $D_3$ components is obtained from early active fractions from the silica gel column which are evaporated to dryness to yield a crude solid mixture of the three components. This crude product is dissolved in 50% aqueous t-butanol and subjected to a reversed phase $C_{18}$ column chromatography. The column is developed with 0.022 M phosphate buffer solution containing an increasing amount of methanol (30%, 40% and 50%). The fractions are examined by TLC and the appropriate fractions purified by preparative HPLC to afford the desired purified components.

It has been discovered that BU-3889V $A_1$ can be converted to BU-3889V $D_1$ by treatment with 1.5N methanolic hydrogen chloride at about 40-60° C. for 1 to 4 days, preferably 2 to 3 days. The desired product is isolated by chromatographic techniques similar to those described above.

In a similar manner, BU-3889V $A_2$ may be converted to BU-3889V $D_2$ and BU-3889V $A_3$ to BU-3889V $D_3$.

BU-3889V $A_1$ can be converted to BU-3889V $A_3$ by reduction, e.g. with sodium borohydride at 25°-° C. Chromatographic techniques are used for isolation and purification of $A_3$.

In a similar manner, BU-3889V $A_2$ may be converted to BU-3889V $D_2$ and BU-3889V $A_3$ to BU-3889V $D_3$.

Physical and Chemical Properties of BU-3s89V $A_1$, BU-3889V $A_2$, BU-3889V $A_3$ and BU-3889V $D_1$ BU-3889V $A_1$, $A_2$ and $A_3$ were isolated as a pale-yellow amorphous powder of weakly acidic nature. They were soluble in water, dimethylformamide and dimethyl sulfoxide, slightly soluble in methanol and acetone but practically insoluble in other organic solvents. BU-3889V $D_1$ was obtained as pale-yellow needles. It was soluble in dimethylformamide and dimethyl sulfoxide but only slightly soluble in water and methanol. Both BU-3889V $A_1$ and $D_1$ showed positive reactions to iodine, ferric chloride, Tollen's and 2,4-dinitrophenylhydrazine, but were negative to ninhydrin, Sakaguchi and Ehrlich tests. BU-3889V $A_1$ was positive to anthrone reagent while BU-3889V $D_1$ was negative in that test. A]l BU-3889V components were labile to light. Upon exposing to fluorescent light at room temperature, they decomposed completely in 4 to 5 days. The physicochemical properties of the four components are summarized in Table 5. The UV spectra of the components were quite similar, exhibiting the maxima at around 238 and 302 nm in water or methanol and no shift was observed in acidic or alkaline media. The IR spectra of BU-3889V $A_1$, $A_2$, $A_3$ and $D_1$ are shown in FIGS. 6 to 9.

The molecular weights of $A_1$ and $D_1$ were determined by negative fast-atom bombardment mass spectrometry (JEOL JMS-SX 102, matrix: glycerol+thioglycerol). Those of $A_2$ and $A_3$ were assigned on the basis of their structural differences from $A_1$ as revealed by their $^1$H- and $^{13}$C-NMR.

The products of the invention show a shift in IR spectra when treated with dilute sodium hydroxide indicating that sodium salts and other metallic salts can be formed. Such salts are within the scope of the invention.

TABLE 5A

Physico-chemical properties of BU-3889V $A_1$ and $A_2$

| | $A_1$ | $A_2$ |
|---|---|---|
| Nature: | Pale-yellow powder | Pale-yellow powder |
| M.P.: | >250° C. | >250° C. |
| $[\alpha]_D^{25}$: | +180° | +108° |
| | (c 0.56, H$_2$O) | (c 0.55, H$_2$O) |
| Negative: | m/z 1541 (M − 2H + K)$^-$ | |
| FAB-MS: | 1525 (M − 2H + Na)$^-$, | |
| | 1563 (M − 3H + K + Na)$^-$ | |
| Mol. wt.: | 1504 | 1506 |
| Elemental: | found | found |
| analysis | C 52.20% | C 53.23% |
| | H 5.06 | H 5.22 |
| UV$_{\lambda max}^{nm}$ ($\epsilon$): | | |
| in H$_2$O | 238 (84,000) | 238 (74,100) |
| | 302 (56,300) | 302 (59,600) |
| in 0.01N HCl | 238 (71,500) | 237 (72,700) |
| | 304 (49,000) | 303 (55,900) |
| in 0.01N NaOH | 238 (79,300) | 237 (76,900) |
| | 302 (53,800) | 302 (59,800) |
| IR (KBr): | 3420, 1710, 1620 | 3410, 1710, 1620 |
| cm$^{-1}$ | 1550, 1450, 1150 | 1550, 1450, 1140 |
| | 1100–1000 | 1100–1000 |
| TLC, SiO$_2$: | Rf 0.05 | 0.05 |
| (n-BuOH-n-PrOH-CONC.NH$_4$OH—H$_2$O = 3:3:1:1) | | |
| TLC, RP-18: | Rf 0.22 | 0.43 |
| (Merck: MeOH-0.022M Phosphate buffer, pH 7.0, 50:50) | | |
| HPLC: | Rt 11.6 min | 6.8 min |
| (Capcell pak C18, MeOH-0.05M Sorensen buffer, pH 8.0, 30–55% gradient) | | |

Capcell pak C18 is a silicon-coated spherical silica gel available from Shiseido, Japan.
RP-18 is a precoated reversed phase silica gel thin layer plate available from Merck.

TABLE 5B

Physico-chemical properties of BU-3889V $A_3$ and $D_1$

| | $A_3$ | $D_1$ |
|---|---|---|
| Nature: | Pale-yellow powder | Pale-yellow needles |
| M.P.: | >250° C. | >250° C. |
| $[\alpha]_D^{25}$: | +36° | +34° |
| | (c 0.55, H$_2$O) | (c 0.5, Pyridine) |
| Negative: | | m/z 1217 (M − 2H + K)$^-$ |
| FAB-MS: | | 1239 (M − 3H + K + Na)$^-$, |
| | | 1201 (M − 2H + Na)$^-$ |
| Mol. wt.: | 1508 | 1180 |
| Elemental: | found | found |

TABLE 5B-continued

Physico-chemical properties of BU-3889V $A_3$ and $D_1$

| | $A_3$ | $D_1$ |
|---|---|---|
| analysis | C 52.64% | C 52.28% |
| | H 5.30 | H 5.42 |
| UV$_{\lambda max}^{nm}$ ($\epsilon$): | | |
| in H$_2$O | 237 (74,200) | 235 (66,000) |
| | 301 (64,900) | 302 (52,500) |
| in 0.01N HCl | 237 (62,000) | 232 (51,600) |
| | 302 (56,300) | 306 (46,600) |
| in 0.01N NaOH | 238 (69,900) | 237 (66,000) |
| | 302 (60,600) | 301 (52,500) |
| IR (KBr): | 3410, 1710, 1620 | 3430, 1710, 1620 |
| cm$^{-1}$ | 1550, 1440, 1150 | 1550, 1455, 1380 |
| | 1100–1000 | 1080, 1000, 800 |
| TLC, SiO$_2$: | Rf 0.05 | 0.34 |
| (n-BuOH-n-PrOH-CONC.NH$_4$OH—H$_2$O = 3:3:1:1) | | |
| TLC, RP-18: | Rf 0.55 | 0.10 |
| (Merck: MeOH-0.022M Phosphate buffer, pH 7.0, 50:50) | | |
| HPLC: | Rt 4.2 min | 17.9 min |
| (Capcell pak C18, MeOH-0.05M Sorensen buffer, pH 8.0, 30–55% gradient) | | |

Capcell pak C18 is a silicon-coated spherical silica gel available from Shiseido, Japan.
RP-18 is a precoated reversed phase silica gel thin layer plate available from Merck.

Physico-chemical Properties of BU-3889V $D_2$ and BU-3889V $D_3$

Figure 16:
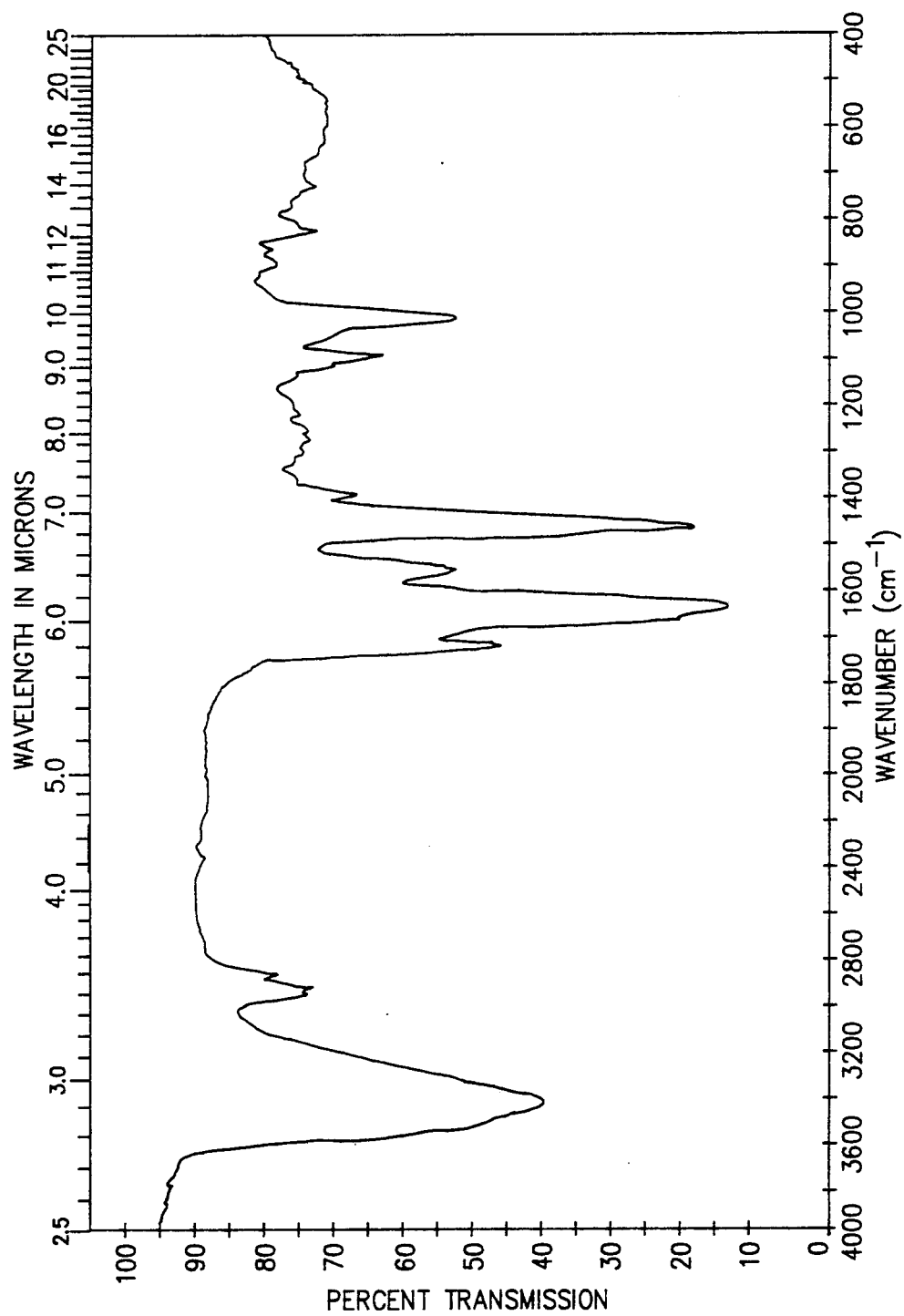
FIGS. 16 and 17 show the infrared (IR) absorption spectrograph of components D2 and D3, respectively, in a potassium bromide pellet.
Figure 17:
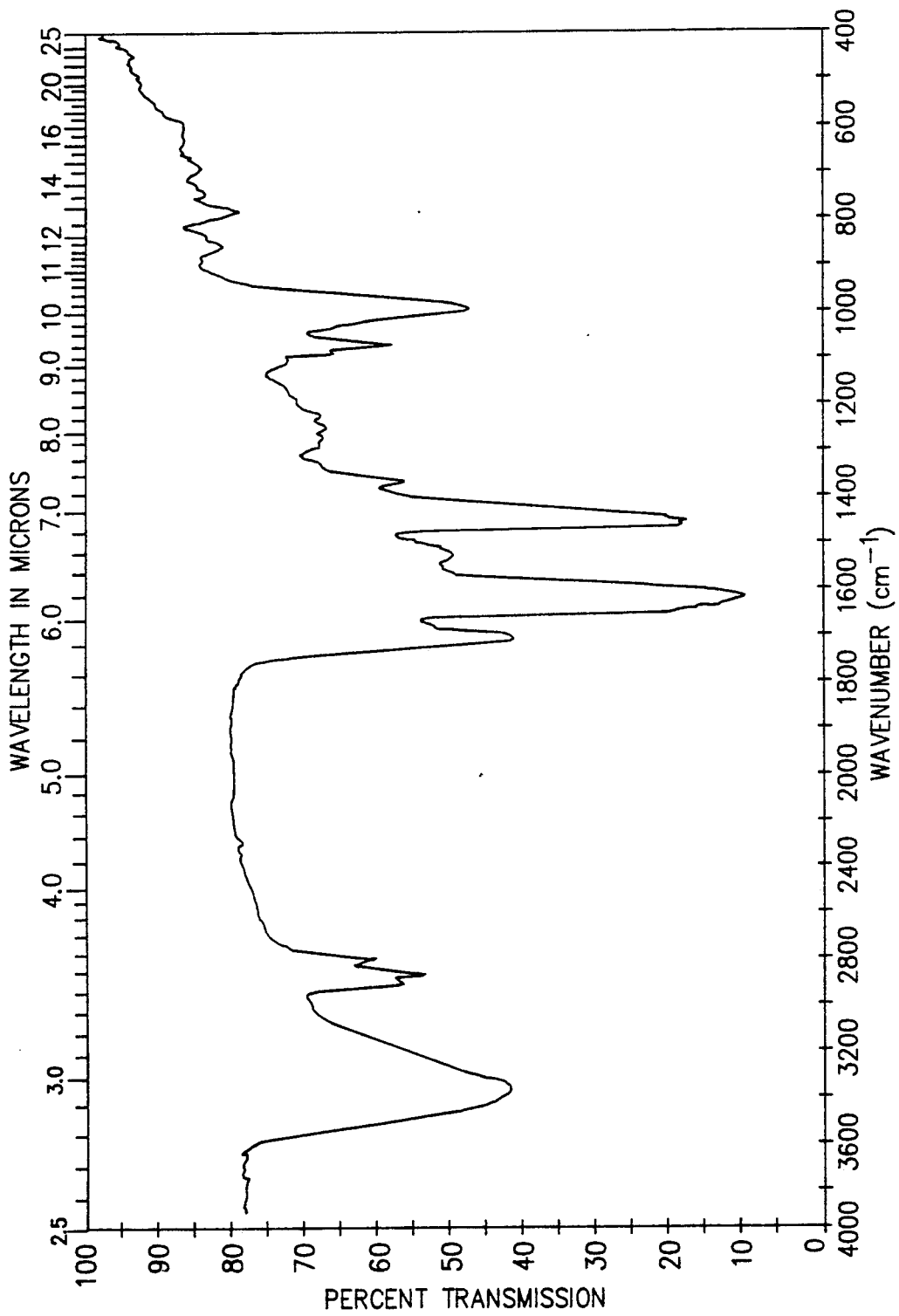
Figure 18:
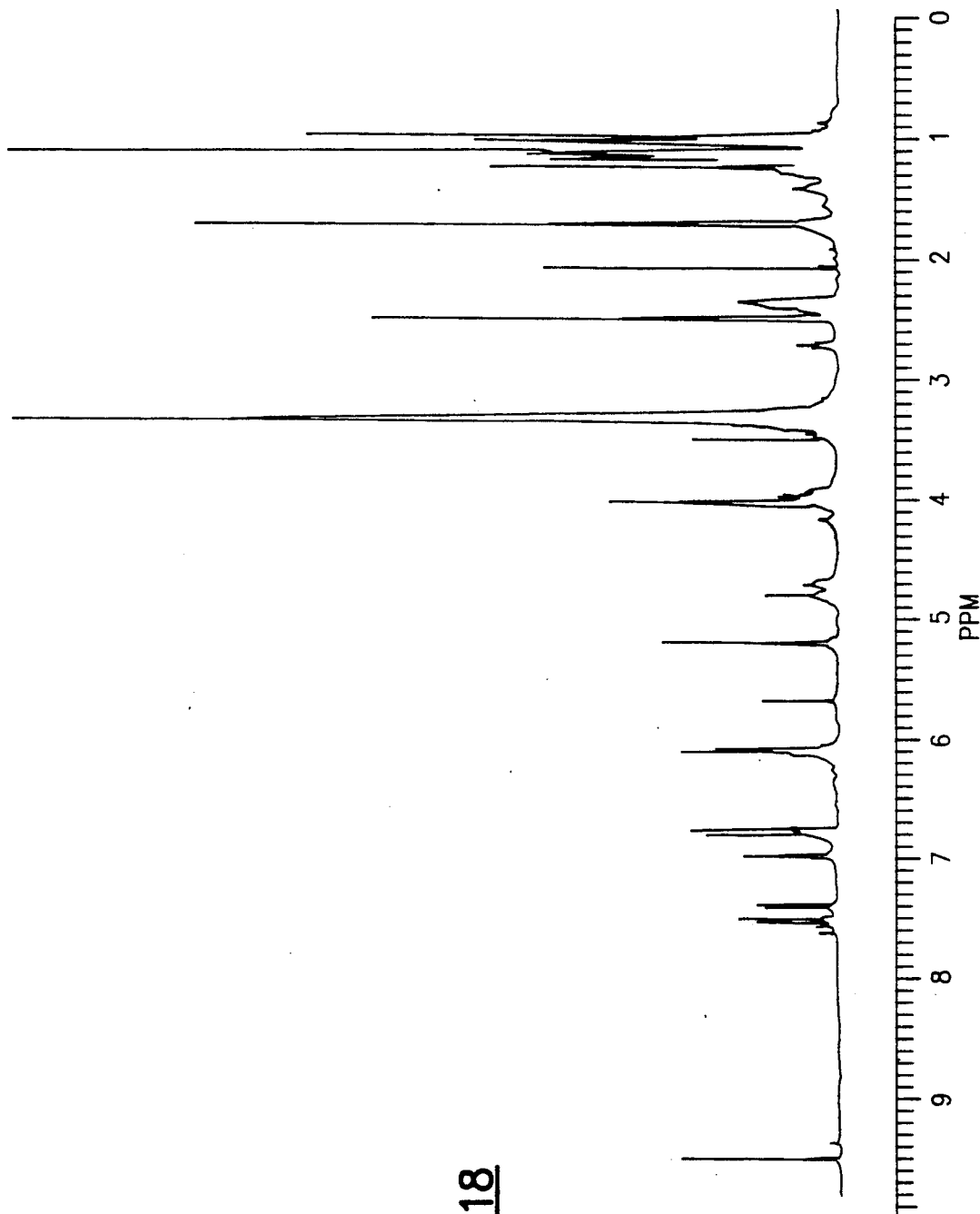
FIGS. 18 and 19 show the $^1$H-NMR spectra of components $D_2$ and $D_3$, respectively.
Figure 19:
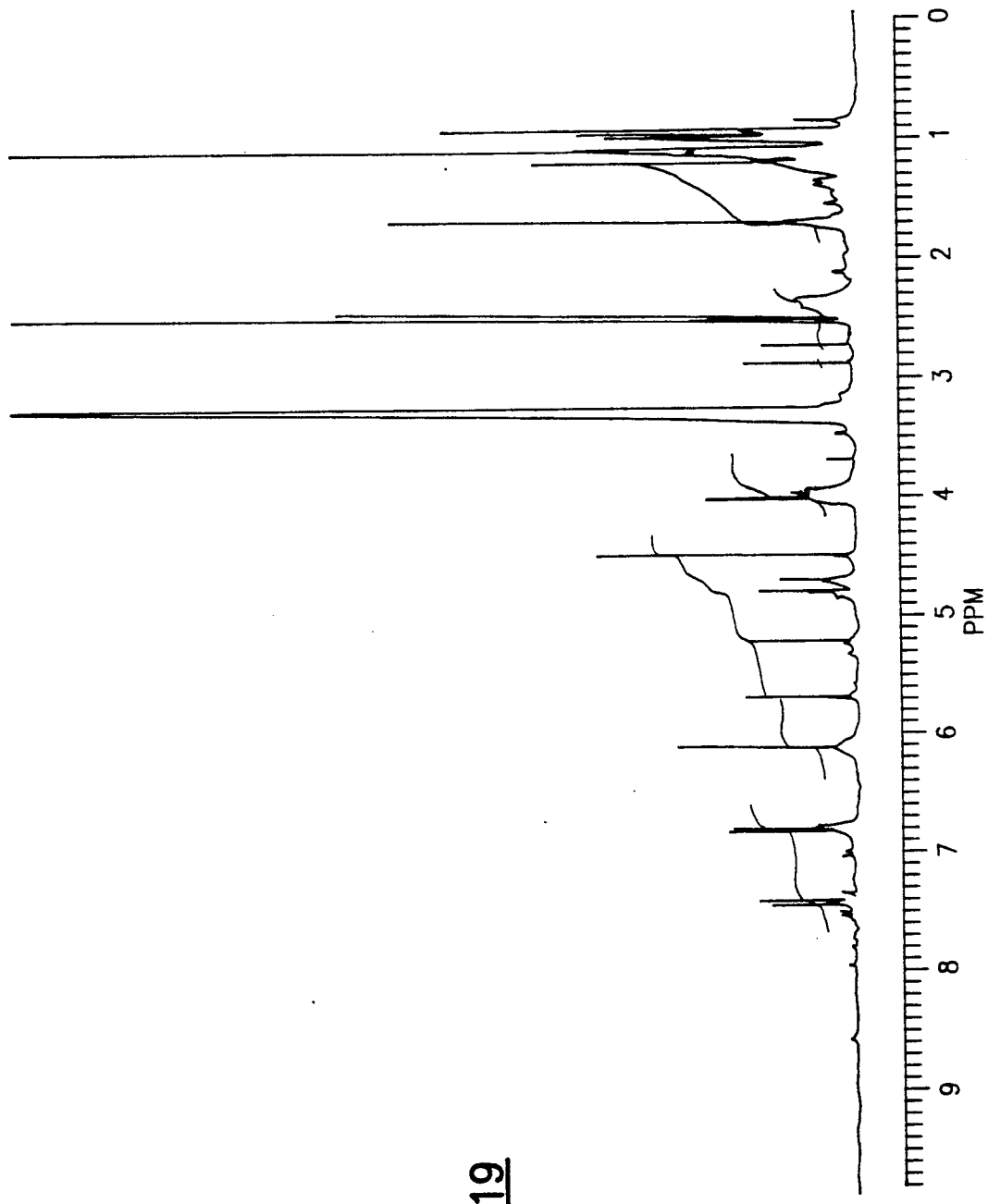

BU-3889V $D_2$ and $D_3$ were obtained as a pale-yellow amorphous powder. The $D_2$ and $D_3$ components had the same solubility, color test and light stability properties as component $D_1$. They showed physico-chemical properties similar to each other and also to those of BU-3889V $D_1$ (Table 6). The molecular weights were suggested to be 1182 for BU-3889V $D_2$ and 1184 for BU-3889V $D_3$ by negative FAB-MS. The IR spectra of BU-3889V $D_2$ and $D_3$ are shown in FIGS. 16 and 17 and their $^1$H-NMR spectra are shown in FIGS. 18 and 19 respectively. Table 7 shows the $^1$H— and $^{13}$C-NMR data of BU-3889V $D_3$.

TABLE 6

Physico-chemical properties of BU-3889V $D_2$ and $D_3$

| | BU-3889V $D_2$ | BU-3889V $D_3$ |
|---|---|---|
| Nature: | Pale-yellow powder | Pale-yellow powder |
| M.P.: | >250° C. | >250° C. |
| $[\alpha]_D^{26}$: | −13° | −17° |
| | (C 0.4, pyridine) | (C 0.4, pyridine) |
| Negative FAB-MS: | m/z 1219 | m/z 1205 (M − 2H + Na)-1221 |
| | (M − 2H + K)$^-$ | (M − 2H + K)$^-$ |
| Mol. wt.: | 1182 | 1184 |
| Elemental: | Found | Found |
| analysis | C 52.47% | C 58.54% |
| | H 4.97 | H 5.80 |
| UV$_{\lambda max}^{nm}$ ($\epsilon$): | | |
| in H$_2$O | 237 (62,200) | 237 (54,200) |
| | 301 (50,400) | 300 (47,200) |
| in 0.01N HCl | 237 (52,000) | 237 (41,000) |
| | 302 (42,900) | 301 (37,900) |
| in 0.01N NaOH | 237 (65,400) | 237 (57,100) |
| | 301 (49,900) | 300 (45,200) |
| IR (KBr) cm$^{-1}$: | 3420, 1710, 1630 | 3420, 1720, 1620 |
| | 1550, 1450, 1080, | 1540, 1455, 1080, |
| | 1000 | 1000 |
| TLC, SiO$_2$: | Rf 0.30 | 0.28 |
| (n-BuOH-n-PrOH-conc. NH$_4$OH—H$_2$O = 3:3:1:1) | | |
| TLC, RP-18: | Rf 0.14 | 0.18 |
| (Merck: MeOH-0.022M phosphate buffer, pH 7.02, 50:50) | | |
| HPLC: | Rt 12.52 min | 9.55 min |
| (Capcell pak C18, MeOH-0.05M Sörensen buffer, pH 8.0, 30–55% gradient) | | |

TABLE 7

$^1$H and $^{13}$C-NMR data of BU-3889V $D_1$

| $^1$H-NMR data (DMSO-$d_6$) | | $^{13}$C-NMR data (DMSO-$d_6$) | |
|---|---|---|---|
| δ | 7.40 (1H. d. J=15.4) | δ | 197.3 s |
| | 6.79 (1H. d. j=15.4) | | 193.9 s |
| | 6.75 (1H. br-d. j=8.1) | | 193.7 s |
| | 6.10 (2H. m) | | 182.3 s |
| | 5.67 (1H. s) | | 174.7 s |
| | 5.21 (1H. s) | | 173.9 s |
| | *4.81 (1H. m) | | 146.3 d |
| | *4.71 (1H. m) | | 145.6 d |
| | *4.51 (1H. s) | | 141.4 s |
| | ca. 4.0 (4H. m) | | 139.4 s |
| | 2.50 (1H. m) | | 133.7 d |
| | 2.39 (2H. m) | | 133.3 s |
| | 1.71 (3H. s) | | 125.9 d |
| | 1.70 (1H. m) | | 125.7 d |
| | 1.50 (1H. m) | | 125.1 d |
| | 1.40 (1H, m) | | 124.3 d |
| | 1.23 (3H. s) | | 96.8 s |
| | 1.11 (3H. d. j=7.3) | | 94.1 s |
| | 1.00 (3H. d. j=6.8) | | 84.8 s |
| | 0.96 (3H. s) | | 84.4 s |
| | | | 63.6 t |
| | | | 62.4 t |
| | | | 43.9 s |
| | | | 43.6 s |
| | | | 36.1 t |
| | | | 34.5 t |
| | | | 27.6 d |
| | | | 27.3 d |
| | | | 26.7 q |
| | | | 21.7 q |
| | | | 20.5 q |
| | | | 19.1 q |
| | | | 12.2 q |

*exchangeable with $D_2O$

Antiviral Activity of BU-3889V $A_1$, BU-3889V $A_2$, BU-3889V $A_3$ and BU-3889V $D_1$ 1. Antiviral activity against heroes simplex virus type 1 and influenza virus A In vitro antiviral activity of BU-3889V was assessed using the herpes simplex virus type 1 (HSV-1)-Vero cell and influenza virus A-Madin Darby canine kidney (MDCK) cell systems by dye-uptake assay method (Antiviral Research 3 223–234, 1986). A 200 μl aliquot of cell suspension containing $2 \times 10^4$ cells was inoculated to each well of 96-well microplates and cultured at 37° C. for 48–72 hours under humidified 5% $CO_2$-95% air. Thereafter, the growth medium was replaced by 250 μl of a fresh medium containing a test compound, to which a 50 μl medium containing approximately $10 \times TCID_{50}$ of virus was added. After 72 hours incubation, the degree of inhibition of viral-induced cytopathic effect and drug-induced cytotoxicity were determined. $ID_{50}$ was expressed as the concentration showing 50% inhibition of cytopathic effect of control and $TD_{50}$ was the concentration exhibiting 50% cytotoxicity against Vero or MDCK cell without viral infection. Acyclovir and ribavirin were used as the reference compounds of anti-HSV activity and anti-influenza virus A activity, respectively. The results are shown in Table 8. BU-3889V $A_1$, $A_2$ and $A_3$ exhibited antiviral activity against HSV with $ID_{50}$ Values of 11 μg/ml and BU-3889V $D_1$ exhibited antiviral activity against influenza virus type A with an $ID_{50}$ value of 6.8 μg/ml.

TABLE 8

Antiviral activity against herpes simplex virus type 1 and influenza virus A

| | HSV-Vero cell | | Influenza virus-MDCK cell | |
|---|---|---|---|---|
| | $ID_{50}$ (μg/ml) | $TD_{50}$ (μg/ml) | $ID_{50}$ (μg/ml) | $TD_{50}$ (μg/ml) |
| BU-3889V $A_1$ | 11 | >400 | 150 | 250 |
| BU-3889V $A_2$ | 11 | >200 | >150 | 150 |
| BU-3889V $A_3$ | 11 | >200 | 88 | 180 |
| BU-3889V $D_1$ | 92 | >200 | 6.8 | 160 |
| Acyclovir | 0.09 | >100 | | |
| Ribavirin | | | 15 | >200 |

2. Anti-HIV activity

Anti-HIV activity was evaluated using the human T-lymphotropic virus type III B (HTLV-IIIB) and HTLV-type I carrying, MT-4 cells. The number of viable MT-4 cells infected with HIV at a multiplicity of infection of 0.002, decreased during the cultivation and almost all cells died within 6 days after infection as determined by a trypan blue dye exclusion method (Antimicrob. Agents and Chemother. 30 933–37, 1986).

Cell damage induced by HIV was significantly inhibited by BU-3889V $A_1$ and $D_1$ at concentration higher than 25 μg/ml of BU-3889V $A_1$ and $D_1$.

Figure 10:
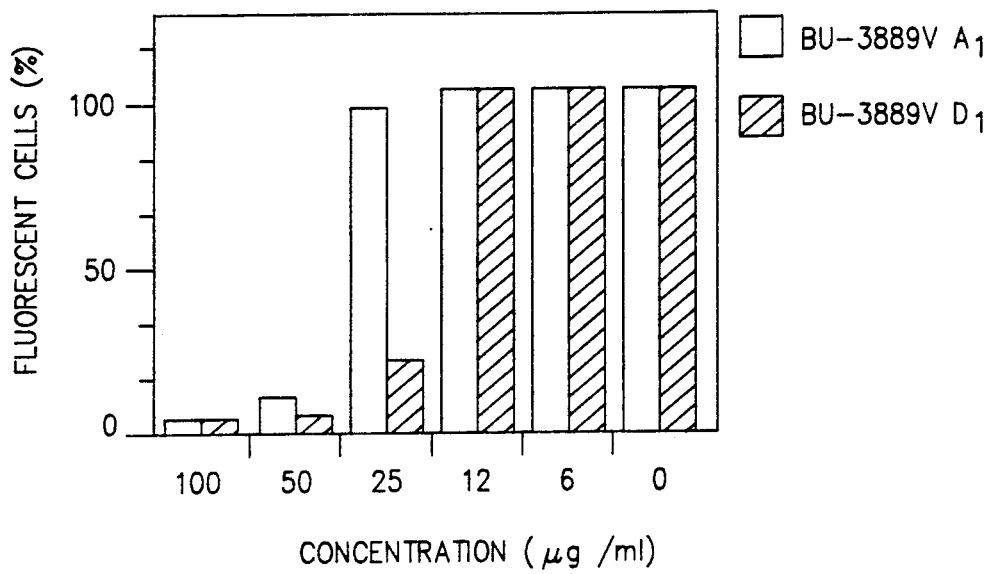
FIG. 10 shows the effect of $A_1$ and $D_1$ on the expression of HIV antigen in infected cells.

Expression of HIV antigen was examined by immunofluorescence. When MT-4 cells were infected with HIV, viral antigen positive cells increased with incubation time and all the cells became positive on day 6 after infection. HIV antigen positive cells were significantly suppressed when HIV-infected MT-4 cells were cultured in the presence of BU-3889V $A_1$ and $D_1$, and positive cells were only less than 1% at the concentration higher than 50 μg/ml of the compounds (FIG. 10).

Inhibitory activity of BU-3889V $A_1$ and $D_1$ on reverse transcriptase (RTase) derived from avian myeloblastosis virus (AMV) was examined. Concentrations higher than 3 μg/ml of BU-3889V $A_1$ and $D_1$ inhibited 1 unit of AMV RTase activity more than 95% (Table 9).

TABLE 9

Effect of BU-3889V $A_1$ and $D_1$ on the AMV reverse transcriptase activity

| Compound Concentration (μg/ml) | BU-3889V $A_1$ | BU-3889V $D_1$ |
|---|---|---|
| 100 | 159 ± 14[a] (99.7)[b] | 185 ± 66 (99.6) |
| 50 | 235 ± 73 (99.5) | 198 ± 80 (99.6) |
| 25 | 621 ± 402 (98.8) | 134 ± 55 (99.8) |
| 12.5 | 920 ± 271 (98.2) | 116 ± 14 (99.8) |
| 6 | 976 ± 145 (98.1) | 287 ± 98 (99.4) |
| 3 | 1,584 ± 1,292 (96.9) | 785 ± 69 (98.5) |
| 0 (Control) | 51,494 ± 1,865 | |

[a] count (cpm)
[b] % inhibition

Antiviral Activity of BU-3889V $A_3$, $D_2$ and $D_3$ against herpes simplex virus type 1 and influenza virus A The in vitro antiviral activity of BU-3889V $A_3$, $D_2$ and $D_3$ was assessed using the herpes simplex virus type 1 (HSV-1)-Vero cell and influenza virus A-Madin Darby canine kidney (MDCK) cell system by the dye-uptake assay (Antiviral Research 3, p. 223–234, 1986). A 200 μl aliquot of cell suspension containing $2 \times 10^4$ cells was inoculated to each well of 96-well microplates and cultured at 37° C. for 48–72 hours under humidified 5% $CO_2$–95% air. Thereafter, the growth medium was replaced by 250 μl of a fresh medium containing a test compound, to which a 50 μl medium containing approximately $10 \times TCID_{50}$ of virus was added. After 72 hours incubation, the degree of inhibition of viral-induced cytopathic effect and drug-induced cytotoxicity were determined. $ID_{50}$ was expressed as the concentration showing 50% inhibition of cytopathic effect of control and $TD_{50}$ was the concentration exhibiting 50% cytotoxicity against Vero or MDCK cells without viral infection. Acyclovir and ribavirin were used as the reference compounds of anti-HSV activity and anti-influenza virus A activity, respectively. The results are shown in Table 10.

TABLE 10
Antiviral activity against herpes simplex virus type 1 and influenza virus A

|  | HSV-Vero cell | | Influenza virus-MDCK cell | |
| --- | --- | --- | --- | --- |
|  | $ID_{50}$ (μg/ml) | $TD_{50}$ (μg/ml) | $ID_{50}$ (μg/ml) | $TD_{50}$ (μg/ml) |
| BU-3889V $D_2$ | 35 | >100 | 9.9 | 68 |
| BU-3889V $D_3$ | 20 | >100 | 24 | >100 |
| BU-3889V $A_3$ | 6.3 | >100 | 41 | 100 |
| Acyclovir | 0.09 | >100 | | |
| Ribavirin | | | 9.5 | >100 |

Anti-HIV activity of BU-3889V $A_1$, $A_2$ and $A_3$

The in vitro anti-HIV activity of BU-3889V $A_1$, $A_2$ and $A_3$ was evaluated in the p24gag antigen capture assay using CEM-F cells. AZT was included as a reference compound. The methodology used in this assay is described below:

Methodology

Cells and Virus

The cells and the virus were grown in LAV/CEM medium. The medium consists of RPMI 1640, supplemented with 1% L-glutamine, 100 U/ml of Penicillin, 100 μg/ml Streptomycin, 2 μg/ml Polybrene and 10% heat-inactivated fetal bovine serum (HyClone Labs). CEM cells were originally derived from acute human lymphoblastic leukemia and represent an established T lymphoblastoid cell line. The LAV/BRU of human immunodeficiency virus (HIV) was obtained from Dr. L. Montagnier, Institute Pasteur, Paris, France. The virus was adapted to CEM cells, and infectious virus stocks were stored as cell-free supernatant fluids in 1 ml aliquots in liquid nitrogen. The titer of the stock was determined by an end point titration method using CEM cells in 96-well microtiter plates. The titration was done with ten replicates for each point, and the 50% tissue culture infective dose ($TCID_{50}$) was calculated using the method of Reed and Muench (Amer. J. Hygiene, 27/3 (1938) 493–497).

Inhibition of HIV Replication

25 The CEM cells ($1.5 \times 10^5$ cells/ml) were placed in 96-well plates and incubated with virus for 45 minutes. After 45 minutes each compound was added in quadruplicate. At the end of the day, six supernatants were tested for presence of viral core protein p24gag in an antigen capture ELISA (Genetic Systems Company).

The OD readings (absorbance at 450/630 nm) fall into three categories: Experimentals = values from wells containing cells, viral inoculum and drug; Controls = values from wells with cells and virus (100%); and Background = values from wells with viral inoculum alone. The background value was subtracted from all the experimental ODs. The antiviral effect is expressed as infective or effective dose 50 ($ID_{50}$ or $ED_{50}$) and represents the amount of drug necessary to reduce the viral replication by 50% as measured through p24gag binding.

Analysis of Cytotoxicity

The toxicities of the drugs were tested against uninfected CEM cells. The CEM cells were plated as described above, and culture for five days in the presence or absence of drugs. On day five 1 μCi/well of $^3H$-thymidine was added, and cells were harvested 3 hours later. The results are expressed as toxic dose 50 ($TD_{50}$) and represent the amount of drug necessary to reduce the cell proliferation by 50% as measured through thymidine incorporation. The results of the assay are shown in Table Table 11.

TABLE 11
Anti-HIV activity using p24gag antigen capture assay

| Compound | μg $ED_{50}$ | μg $TD_{50}$ |
| --- | --- | --- |
| BU-3889V $A_1$ | 3.2 | >100 |
| BU-3889V $A_2$ | 2.5 | >100 |
| BU-3889V $A_3$ | 6.8 | 95 |
| AZT | 0.055 | 4.2 |

Anti-HIV activity of BU-3889V $D_2$ and $D_3$

The BU-3889V components were evaluated for activity against human immunodeficiency virus ($LAV_{BRU}$ strain obtained from Luc Montagnier, Institut Pasteur, Paris, France) in CEM-SS cells (P. L. Nara et al. in AIDS Res. Human Retroviruses, 1987, 3, 283–302) using the XTT assay described by D. S. Weislow, et al. in J. Natl. Cancer Institut., 1989, 81, 577–586. CEM-SS cells were obtained from Owen Weislow at the National Cancer Institute.

The antiviral effect is expressed as the concentration of compound which increases the number of viable cells in infected cultures to 50% that of the untreated, uninfected control cultures ($ED_{50}$). The cellular toxicity is expressed as the concentration of compound which reduces the number of viable cells to 50% that of the untreated control ($TD_{50}$). Table 12 shows the results of this assay.

TABLE 12
Anti-HIV activity of BU-3889V components in CEM-SS cells evaluated by XTT assay six days post infection

| Compound | μg/ml $ED_{50}$ | μg/ml $TD_{50}$ |
| --- | --- | --- |
| BU-3889V $A_1$ | 20 | 300 |
| BU-3889V $A_2$ | 10 | 200 |
| BU-3889V $A_3$ | 25 | 600 |
| BU-3889V $D_1$ | 20 | >500 |
| BU-3889V $D_2$ | 20 | >500 |
| BU-3889V $D_3$ | 10 | 100 |
| AZT | 0.005 | >500 |

Methods of Use and Pharmaceutical Compositions

The antiviral antibiotic complex, BU-3889V and its components $A_1$, $A_2$, $A_3$, $D_1$, $D_2$ and $D_3$ according to the present invention and pharmaceutical compositions thereof are useful to inhibit the growth of viruses, including the herpes simplex and influenza viruses. These antiviral effects are demonstrated and described above. In addition, BU-3889V $A_1$, $A_2$, $A_3$, $D_1$, $D_2$ and $D_3$ are useful in the inhibition of HIV virus.

In general, the antibiotics of the invention may be administered orally or parenterally in pure solid form, in dilute solutions or suspensions or in concentrates and prepared for unit dose or multi-dose presentation. When administered parenterally, by intravenous or intramuscular or subcutaneous injection, or when administered orally, the dosage administration will be dependent on the age and weight of the mammalian species being treated, the route of administration, and the type and severity of the infectious condition being treated and other factors readily evaluated by the physician or veterinarian in attendance.

In respect to pharmaceutical compositions containing the antibiotics herein, carrier and other ingredients should be such as not to diminish the therapeutic effects of the antibiotic. Suitable dosage forms for oral use are tablets, dispersible powders, granules, capsules, syrups and elixirs. Examples of parenteral forms are solutions, suspensions, dispersions, emulsions, and the like. The compositions for oral use may contain one or more conventional adjuvants, such as sweetening agents, flavoring agents, coloring agents and preserving agents, in order to provide a composition of suitable pharmaceutical elegance. Tablets may contain the active ingredient in admixture with conventional pharmaceutically acceptable excipients including inert diluents such as calcium carbonate, sodium carbonate, lactose and talc; granulating and disintegrating agents such as starch and alginic acid; binding agents such as starch, gelatin and acacia and lubricating agents such as magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs may contain the active ingredients in admixture with any of the conventional excipients utilized for the preparation of such compositions such as suspending agents (e.g., methylcellulose, tragacanth, and sodium alginate), wetting agents (e.g., lecithin, polyoxyethylene stearate) and preservatives such as ethyl p-hydroxybenzoate. Capsules may contain the active ingredient alone or admixed with an inert solid diluent such as calcium carbonate, calcium phosphate and kaolin. The injectable compositions are formulated as shown in the art and may contain appropriate dispersing or wetting agents and suspending agents identical or similar to those mentioned above.

The daily dosage for adult human treatment will preferably range from about 100 mg to about 1,000 mg of the selected therapeutic agent for a 70 kg adult, depending on the nature of the infection and the frequency and route of administration inter alia. It will be appreciated that in some instances, e.g. in the treatment of neonates, infants and juveniles, smaller dosages than adult dosages may be desired.

The pharmaceutical compositions of this invention thus will generally comprise a growth inhibitory amount (i.e. an amount effective to inhibit the growth of the virus causing the condition of infection to be treated) of BU-3889V or its components in a suitable pharmaceutically acceptable carrier such as water or alcohols which may contain fillers, stabilizers, wetting agents, emulsifying agents and dispersing agents to name but a few conventional carriers, adjuvant and excipients which may be employed.

The following examples are given by way of illustration only and are not to be considered limitations of this invention, many apparent variations of which are possible without departing from the spirit and scope thereof.

EXAMPLE 1

A piece of the mature slant culture of *Amycolatopsis orientalis* ATCC-53884 was inoculated into a 500-ml Erlenmeyer flask containing 100 ml of a seed medium comprising soluble starch (Nichiden Kagaku) 0.5%, glucose 0.5%, fish meat extract (Mikuni) 0.1%, NZ-case (Sheffield) 0.2%, NaCl 0.2% and $CaCO_3$ 0.1% (pH 7.0). The seed culture was incubated at 32° C. for 4 days on a rotary shaker (200 rpm). A five-milliliter portion of the above seed culture was transferred into a 500-ml Erlenmeyer flask containing 100 ml of a fermentation medium composed of soluble starch 2%, beet molasses (Nihon Tensai Seito) 1% and $CaCO_3$ 0.5% (pH 7.0). Fermentation was carried out at 28° C. for 7 days on a rotary shaker (200 rpm). The antibiotic production in the fermentation broth was determined by the dye-uptake assay method using herpes simplex virus type 1.

The fermentation broth showed the antiviral activity at 12× dilution during 4 through 7 day's fermentation. Large scale fermentation of ATCC-53884 was carried out in a tank fermentor (200 L). A two-liter portion of the seed culture prepared by flask fermentation was transferred into a 200-liter tank fermentor containing 120 liters of the production medium having the same composition as the medium which was used in flask fermentation. The tank fermentation was carried out at 32° C. with agitation of 250 rpm and aeration rate of 120 liters per minute.

The fermentation broth (210 L, 50-100 mcg/ml) was centrifuged using a Sharples centrifuge. The clarified supernatant (200 L) was adjusted to pH 7.0 with 6N HCl, stirred vigorously with Diaion HP-20 resin (20 L) for one hour and filtered. The resin was washed with water (30 L) and then 20% aqueous methanol (30 L). Upon monitoring by dye-uptake assay with herpes simplex virus type the activity was eluted with 80% aqueous acetone (pH 8.0, 20 L). Active effluents were combined and concentrated in vacuo to an aqueous solution (4.5 L) which was, after being adjusted to pH 7.0, applied to a column of Diaion HP-20 (2.4 L). The column was developed with water and 80% aqueous methanol (9 L), successively. The bioactive methanolic eluate was evaporated under reduced pressure to an aqueous solution (3.5 L) which was washed with ethyl acetate (1.5 L). The aqueous layer was taken up and concentrated to afford a crude solid of BU-3889V (31.6 g).

All operations described hereafter were conducted in a dark room.

A part of the crude solid obtained above (23.8 g) was mixed with silica gel (130 ml) and loaded on the top of a silica gel column (Wakogel C-200, 350 ml). The column was developed stepwisely with n-BuOH-n-PrOH-conc.$NH_4OH$-$H_2O$, mixture (5:5:1:1, 2L, fr. Nos. 1-20 and 3:3:1:1, 4 L, fr. Nos. 21-66). Eluted fractions (100 ml) were monitored by the antiviral assay and TLC (SiO$_2$; n-BuOH-n-PrOH-conc.NH$_4$OH-H$_2$O, 3:3:1:1; UV and H$_2$SO$_4$ detection). Fractions Nos. 8 and 9 were combined and concentrated in vacuo to yield a crude solid of BU-3889V D$_1$ (410 mg). The second active pools, fractions Nos. 31 to 41, were worked up by the same way to afford a mixture (6.35 g) which was found to contain three components BU-3889V A$_1$, A$_2$ and A$_3$ by HPLC. This solid (390 mg) was dissolved in 4 ml of 0.022M phosphate buffer (pH 7.0) and subjected to a reversed C$_{18}$ column chromatography (YMC-ODS, AM type, Yamamura Chem. Lab. Co., Ltd., 800 ml). The column was developed with the 0.022M phosphate buffer solution containing an increasing amount of methanol (25%, 28%, 30% and 35%) and the eluate was examined by TLC (RP-18, Merck; MeOH-0.022M phosphate buffer, pH 7.0, 50:50). The first active fractions containing component A$_3$ were collected and concentrated to a small volume (30 ml) which was applied to a column of Diaion HP-20 (50 ml). After washing with water, the column was eluted with 80% aqueous methanol to afford a pure solid of BU-3889V A$_3$ (70 mg, 97% purity by HPLC). The second and third active eluates were worked up in a similar fashion to yield purified solids of BU-3889V A$_2$ (87 mg, 97% purity) and A$_1$ (54 mg, 91% purity) respectively. Further purification of BU-3889V A$_1$ (52 mg) was carried out by preparative HPLC (column; Capcell pak C$_{18}$, Shiseido, 30×250 mm, mobile phase; MeOH-0.05M Sörensen buffer, pH 8.0, 30-55% linear gradient, detection; UV 254 nm, flow rate; 5 ml/min). the peak cuts were collected and concentrated to a small volume (35 ml) which was adjusted to pH 7.0 and applied to a column of Diaion HP-20 (80 ml). After washing with water, the column was eluted with 80% aqueous methanol to afford pure solid BU-3889V A$_1$ (39 mg, 98.7% purity).

Purification of BU-3889V D$_1$

The crude solid of component D$_1$ (410 mg) obtained as described above was dissolved in 4 ml of 50% aqueous t-BuOH and applied to a YMC-ODS column (AM type, 800 ml). The column was developed successively with mixture of MeOH-0.022M phosphate buffer, pH 7.0 (20:80, 30:70, 40:60 and 50:50). The fractions (20 ml) were examined by TLC (SiO2: n-BuOH-n-PrOH-conc.NH40H-H20, 3:3:1:1) and the appropriate fractions were concentrated to give semi-pure solid BU-3889V D$_1$ (18 mg, 45% purity). The solid was further purified by preparative HPLC under the same conditions as used for that of BU-3889V A$_1$ to afford pure solid BU-3889V D$_1$ (3.6 mg, 96% purity).

EXAMPLE 2

Preparation of BU-3889V D$_1$ from BU-3889V A$_1$

A solution of BU-3889V A$_1$ (870 mg, 83% purity) in 40 ml of 1.5N methanolic hydrogen chloride was stirred at 50° C. for 2 days. The reaction mixture was neutralized with Amberlite IR-45 (OH−) and concentrated in vacuo. The residue was stirred vigorously with a mixture of n-butanol and water (200 ml each). The n-BuOH layer was taken up and evaporated to dryness. The residue (690 mg) was purified by column chromatography on YMC-ODS (AM-type, 800 ml) to give a purer sample of solid D$_1$ (390 mg, 80% purity). This (80 mg) was finally purified by preparative HPLC to isolate a pure sample of BU-3889V D$_1$ (30 mg) which was identical with the natural product in all respects. This sample was crystallized from a mixture of MeOH-EtOAc to deposit pale-yellow needles of homogeneous BU-3889V D$_1$ (14 mg).

The aqueous layer of the above hydrolyzate was concentrated to a small volume which was charged on a column of Sephadex LH-20 (250 ml). Upon developing with 50% methanol, the anthrone-positive fractions were combined and evaporated to yield a white amorphous solid (60 mg). This product was identified as methyl D-galactoside by a direct comparison with an authentic sample and by optical rotational value [(α)$^{26}$D+72°, c 3.0, H$_2$O].

EXAMPLE 3

Preparation of BU-3889V A$_3$ from BU-3889V A$_1$

To an aqueous ethanolic solution (1:1, 100 ml) of BU-3889V A$_1$ (0.96 g) was added sodium borohydride (1.1 g) with stirring at room temperature. After 3 minutes, the reaction mixture was poured into ice water and the aqueous solution adjusted to pH 7.0 with 6N HCl. The solution was applied on a column of Diaion HP-20 (320 ml) which was washed with water and eluted with 80% aqueous acetone. The eluate containing the product was concentrated in vacuo to give 1.18 g of yellow powder. A portion of the powder (390 mg) was purified by reversed phase column chromatography (YMC-ODS, 680 ml) with stepwise elution of 20-40% methanol in 0.017M Sörensen buffer (pH 7.0) to yield a pure sample (82 mg). It was identical with BU-3889V A$_3$ obtained from the fermentation products in both spectral data and HPLC.

EXAMPLE 4

Isolation of BU-3889V D$_2$ and D$_3$

A portion of the crude solid of BU-3889V D$_1$ (1.47 g) obtained by the general procedure of Example 1 was dissolved in 8 ml of 50% aqueous t-butanol and subjected to a reversed-phase C!s column chromatography (YMC-ODS, AM type, Yamamura Chem. Lab. Co., Ltd., 600 ml). The column was developed with a 0.022M phosphate buffer solution containing an increasing amount of methanol (30%, 40% and 50%) and the eluate was examined by TLC (RP-18, Merck; MeOH-0.022M phosphate buffer, pH 7.0 = 50:50 v/v). The first active fractions (Rf 0.18) were pooled, concentrated in vacuo to a small volume (40 ml) which was applied to a column of Diaion HP-20 (100 ml). After washing with water, the column was eluted with 80% aqueous methanol to afford a semi-pure solid of BU-3889V D$_3$ (260 mg, 53% purity by HPLC). The second (Rf 0.14) and third (Rf 0.10) active fractions were worked up by the same way to yield solids of BU-3889V D$_2$ (154 mg, 48% purity) and BU-3889V D$_1$ (97 mg, 33% purity), respectively. These materials were further purified by preparative HPLC (Column:Capcell pak C$_{18}$, Shiseido, 30×250 mm, mobile phase: MeOH-0.05M Sorensen buffer, pH 8, 30-55% linear gradient, detection: UV 254nm, flow rate: 15/ml/min). The peak cuts containing pure D$_2$ and those containing pure D$_3$ were collected and desalted by a column of Diaion HP-20 to afford reasonably pure solids of BU-3889V D$_2$ (32 mg, 92% purity) and BU-3889V D$_3$ (77 mg, 91% purity) respectively.

EXAMPLE 5

Chemical derivatization of BU-3889V D$_2$ and D$_3$

A. Conversion of BU-3889V A$_2$→D$_2$

BU-3889V A$_2$ (475 mg, 80% purity) dissolved in 40 ml of 1.5 N methanolic hydrogen chloride was stirred at 50° C. for 24 hours. The mixture was neutralized by 6N NaOH and concentrated in vacuo. The concentrate (30 ml) was applied to a column of Diaion HP-20 (100 ml) which was washed with water and eluted with 80% aqueous methanol (250 ml). The active eluate was evaporated to give a light-brown powder (388 mg). This solid was further purified by column chromatography of YMC-ODS (AM type, 800 ml), followed by desalting with Diaion HP-20 to afford a pure sample (173 mg), which was identical in all respects with BU-3889V D$_2$ obtained from the fermentation broth.

B. Conversion of BU-3889V A$_3$→D$_3$

BU-3889V A$_3$ (600 mg, 82%) was hydrolyzed in 1.5N methanolic hydrogen chloride at 50° C. for 24 hours. The reaction solution was worked up as indicated above in Step (A) to afford pure BU-3889V D$_3$ (81 mg). The material was identical with the fermentation-obtained product obtained in Example 4.

What is claimed is:

1. A process for the preparation of antibiotic BU-3889V complex and individual components A$_1$, A$_2$, A$_3$, D$_1$, D$_2$ and D$_3$ which comprises cultivating *Amycolatopsis orientalis* ATCC 53884, a BU-3889V-producing mutant or variant thereof, in an aqueous fermentation culture nutrient medium containing assimilable sources of carbon and nitrogen under submerged aerobic conditions until a substantial amount of antibiotic BU-3889V complex is produced and then recovering the complex.

2. A process for the preparation of BU-3889V A$_1$ which comprises cultivating ATCC 53884, a BU-3889V-producing mutant or variant thereof, in an aqueous nutrient medium containing assimilable sources of carbon and nitrogen under submerged aerobic conditions until a substantial amount of BU-3889V A$_1$ is produced and then recovering the BU-3889V A$_1$ substantially free of co-produced substances.

3. A process for the preparation of BU-3889V A$_2$ which comprises cultivating *Amycolatopsis orientalis* ATCC 53884, a BU-3889V-producing mutant or variant thereof, in an aqueous nutrient medium containing assimilable sources of carbon and nitrogen under submerged aerobic conditions until a substantial amount of BU-3889V A$_2$ is produced and then recovering the BU-3889V A$_2$ substantially free of co-produced substances.

4. A process for the preparation of BU-3889V A$_3$ which comprises cultivating *Amycolaptosis orientalis* ATCC 53884, a BU-3889V-producing mutant or variant thereof, in an aqueous nutrient medium containing assimilable sources of carbon and nitrogen under submerged aerobic conditions until a substantial amount of BU-3889V A$_3$ is produced and then recovering the BU-3889V A$_3$ substantially free of co-produced substances.

5. A process for the preparation of BU-3889V D$_1$ which comprises cultivating *Amycolaptosis orientalis* ATCC 53884, a BU-3889V-producing mutant or variant thereof, in an aqueous nutrient medium containing assimilable sources of carbon and nitrogen under submerged aerobic conditions until a substantial amount of BU-3889V D$_1$ is produced and then recovering the BU-3889V D$_1$ substantially free of co-produced substances.

6. A process for the preparation of BU-3889V D$_2$ which comprises cultivating *Amycolaptosis orientalis* ATCC 53884, a BU-3889V-producing mutant or variant thereof, in an aqueous nutrient medium containing assimilable sources of carbon and nitrogen under submerged aerobic conditions until a substantial amount of BU-3889V D$_2$ is produced and then recovering the BU-3889V D$_2$ substantially free of co-produced substances.

7. A process for the preparation of BU-3889V D$_3$ which comprises cultivating *Amycolaptosis orientalis* ATCC 53884, a BU-3889V-producing mutant or variant thereof, in an aqueous nutrient medium containing assimilable sources of carbon and nitrogen under submerged aerobic conditions until a substantial amount of BU-3889V D$_3$ is produced and then recovering the BU-3889V D$_3$ substantially free of co-produced substances.

* * * * *